US006013644A

United States Patent [19]

Mills et al.

[11] Patent Number: 6,013,644

[45] Date of Patent: Jan. 11, 2000

[54] SPIRO-SUBSTITUTED AZACYCLES AS MODULATORS OF CHEMOKINE RECEPTOR ACTIVITY

[75] Inventors: Sander G. Mills, Scotch Plains; Malcolm Maccoss, Freehold; Martin S. Springer, Westfield, all of N.J.

[73] Assignee: Merck & Co., Inc., Rahway, N.J.

[21] Appl. No.: 08/989,940

[22] Filed: Dec. 12, 1997

Related U.S. Application Data

[60] Provisional application No. 60/032,890, Dec. 13, 1996, and provisional application No. 60/033,535, Dec. 20, 1996.

[51] Int. Cl.[7] ........................ A61K 31/435; A61K 31/54; A61K 31/40; A61K 31/425

[52] U.S. Cl. ........................ 514/210; 514/212; 514/222.2; 514/227.8; 514/228.2; 514/228.8; 514/230.5; 514/241; 514/252; 514/278; 514/361; 514/362; 514/363; 514/364; 514/365; 514/374; 514/381; 514/382; 514/393; 514/394; 514/397; 514/406; 514/409

[58] Field of Search .................................... 514/210, 212, 514/222.2, 227.8, 228.2, 228.8, 230.5, 241, 252, 278, 361, 362, 363, 364, 365, 374, 381, 382, 393, 394, 397, 406, 409

[56] References Cited

FOREIGN PATENT DOCUMENTS

WO 94/17045 8/1994 WIPO .
WO 94/29309 12/1994 WIPO .
WO 96/10568 4/1996 WIPO .

*Primary Examiner*—Frederick Krass
*Attorney, Agent, or Firm*—J. Eric Thies; David L. Rose

[57] ABSTRACT

The present invention is directed spiro-substituted azacycles of formula I:

I

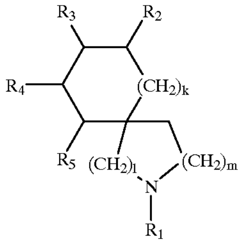

(wherein $R_1$, $R_2$, $R_3$, $R_4$, $R_5$, k, l and m are defined herein) which are useful as modulators of chemokine receptor activity. In particular, these compounds are useful as modulators of the chemokine receptors CCR-1, CCR-2, CCR-2A, CCR-2B, CCR-3, CCR-4, CCR-5, CXCR-3, and/or CXCR-4.

9 Claims, No Drawings

SPIRO-SUBSTITUTED AZACYCLES AS MODULATORS OF CHEMOKINE RECEPTOR ACTIVITY

CROSS REFERENCE TO RELATED APPLICATIONS

This application claims priority under 35 U.S.C. § 119(e) from U.S. Ser. No. 60/032,890, filed Dec. 13, 1996, and U.S. Ser. No. 60/033,535, filed Dec. 20, 1996.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3, 165–183 (1991) and Murphy, *Rev. Immun.*, 12, 593–633 (1994)). There are two classes of chemokines, C-X-C ((α) and C-C (β), depending on whether the first two cysteines are separated by a single amino acid (C-X-C) or are adjacent (C-C). The α-chemokines, such as interleukin-8 (IL-8), neutrophil-activating protein-2 (NAP-2) and melanoma growth stimulatory activity protein (MGSA) are chemotactic primarily for neutrophils, whereas β-chemokines, such as RANTES, MIP-1α, MIP-1β, monocyte chemotactic protein-1 (MCP-1), MCP-2, MCP-3 and eotaxin are chemotactic for macrophages, T-cells, eosinophils and basophils (Deng, et al., *Nature*, 381, 661–666 (1996)).

The chemokines bind specific cell-surface receptors belonging to the family of G-protein-coupled seven-transmembrane-domain proteins (reviewed in Horuk, *Trends Pharm. Sci.*, 15, 159–165 (1994)) which are termed "chemokine receptors." On binding their cognate ligands, chemokine receptors transduce an intracellular signal though the associated trimeric G protein, resulting in a rapid increase in intracellular calcium concentration. There are at least seven human chemokine receptors that bind or respond to β-chemokines with the following characteristic pattern: CCR-1 (or "CKR-1" or "CC-CKR-1") [MIP-1α, MIP-1β, MCP-3, RANTES] (Ben-Barruch, et al., *J. Biol. Chem.*, 270, 22123–22128 (1995); Beote, et al, *Cell*, 72, 415–425 (1993)); CCR-2A and CCR-2B (or "CKR-2A"/"CKR-2A" or "CC-CKR-2A"/"CC-CKR-2A") [MCP-1, MCP-3, MCP-4]; CCR-3 (or "CKR-3" or "CC-CKR-3") [eotaxin, RANTES, MCP-3] (Combadiere, et al., *J. Biol. Chem.*, 270, 16491–16494 (1995); CCR-4 (or "CKR-4" or "CC-CKR-4") [MIP-1α, RANTES, MCP-1] (Power, et al., *J. Biol. Chem.*, 270, 19495–19500 (1995)); CCR-5 (or "CKR-5" or "CC-CKR-5") [MIP-1α, RANTES, MIP-1β] (Sanson, et al., *Biochemistry*, 35, 3362–3367 (1996)); and the Duffy blood-group antigen [RANTES, MCP-1] (Chaudhun, et al., *J. Biol. Chem.*, 269, 7835–7838 (1994)). The β-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma and allergic diseases, as well as autoimmune pathologies such as rheumatoid arthritis and atherosclerosis. For example, the chemokine receptor CCR-3 plays a pivotal role in attracting eosinophils to sites of allergic inflammation. Accordingly, agents which modulate chemokine receptors would be useful in such disorders and diseases.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV.

Certain compounds have been demonstrated to inhibit the replication of HIV, including soluble CD4 protein and synthetic derivatives (Smith, et al., *Science*, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 gyycoprotein of the cell.

Entry of HIV-1 into a target cell requires cell-surface CD4 and additional host cell cofactors. Fusing has been identified as a cofactor required for infection with virus adapted for growth in transformed T-cells, however, fusing does not promote entry of macrophagetropic viruses which are believed to be the key pathogenic strains of HIV in vivo. It has recently been recognized that for efficient entry into target cells, human immunodeficiency viruses require the chemokine receptors CCR-5 and CXCR-4, as well as the primary receptor CD4 (Levy, *N. Engl. J. Med.*, 335(20), 1528–1530 (Nov. 14, 1996). The principal cofactor for entry mediated by the envelope glycoproteins of primary macrophage-trophic strains of HIV-1 is CCR5, a receptor for the β-chemokines RANTES, MIP-1α and MIP-1β (Deng, et al., *Nature*, 381, 661–666 (1996)). HIV attaches to the CD4 molecule on cells through a region of its envelope protein, gp120. It is believed that the CD-4 binding site on the gp120 of HIV interacts with the CD4 molecule on the cell surface, and undergoes confirmation changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. Macrophage-tropic HIV and SIV envelope proteins have been shown to induce a signal through CCR-5 on CD4+ cells resulting in chemotaxis of T cells which may enhance the replication of the virus (Weissman, et al., *Nature*, 389, 981–985 (1997)). It has been shown that β-chemokine ligands prevent HIV-1 from fusing with the cell (Dragic, et al., *Nature,* 381, 667–673 (1996)). It has further been demonstrated that a complex of gp120 and soluble CD4 interacts specifically with CCR-5 and inhibits the binding of the natural CCR-5 ligands MIP-1α and MIP-1β (Wu, et al., *Nature*, 384, 179–183 (1996); Trkola, et al., *Nature*, 384, 184–187 (1996)).

Humans who are homozygous for mutant CCR-5 receptors which do not serve as co-receptors for HIV-1 in vitro apper to be unusually resistant to HIV-1 infection and are not immuno-compromised by the presence of this genetic variant (*Nature*, 382, 722–725 (1996)). Similarly, an alteration in the CCR-2 gene, CCR2-641, can prevent the onset of full-blown AIDS (Smith, et al., *Science*, 277,959–965 (1997). Absence of CCR-5 appears to confer protection from HIV-1 infection (*Nature*, 382, 668–669 (1996)). An inherited mutation in the gene for CCR5, Delta 32, has been shown to abolish functional expression of the gene and individuals homozygous for the mutation are apparently not susceptible to HIV infection. Other chemokine receptors may be used by some strains of HIV-1 or may be favored by non-sexual routes of transmission. Although most HIV-1 isolates studied to date utilize CCR-5 or fusing, some can use both as well as the related CCR-2B and CCR-3 as co-receptors (*Nature Medicine*, 2(11), 1240–1243 (1996)). Nevertheless, drugs targeting chemokine receptors may not be unduly compromised by the genetic diversity of HIV-1 (Zhang, et al., *Nature*, 383, 768 (1996)). The β-chemokine macrophage-derived chemokine (MDC) has been shown to inhibit HIV-1 infection (Pal, et al., *Science*, 278 (5338), 695–698 (1997). The chemokines RANTES, MIP-1α, MIP-1β, vMIP-I, vMIP-II, SDF-1 have also been shown to suppress HIV. A derivative of RANTES, (AOP)-RANTES, is a subnanomolar antagonist of CCR-5 function in monocytes (Simmons, et al., *Science*, 276,276–279 (1997)). Monoclonal antibodies to CCR-5 have been reported to block infection of cells by HIV in vitro. Accordingly, an agent which could block chemokine receptors in humans who possess normal chemokine receptors should prevent infection in healthy individuals and slow or halt viral progression in infected patients (see *Science*, 275, 1261–1264 (1997)). By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1α, MIP-1β, MCP-1, and MCP-3 are known to bind to chemokine receptors. As noted above, the inhibitors of HIV-1 replication present in supernatants of CD8+ T cells have been characterized as the β-chemokines RANTES, MIP-1α and MIP-1β. PCT Patent Publications WO 94/17045 (published Aug. 4, 1994), WO 94/29309 (published Dec. 22, 1994), and WO 96/10568 (published Apr. 11, 1996) disclose certain spiro-substituted azacycles as tachykinin antagonists.

SUMMARY OF THE INVENTION

The present invention is directed to compounds which are modulators of chemokine receptor activity and are useful in the prevention or treatment of certain inflammatory and immunoregulatory disorders and diseases, including asthma and allergic diseases, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

The present invention is further concerned with compounds which inhibit the entry of human immunodeficiency virus (HIV) into target cells and are of value in the prevention of infection by HIV, the treatment of infection by HIV and the prevention and/or treatment of the resulting acquired immune deficiency syndrome (AIDS). The present invention also relates to pharmaceutical compositions containing the compounds and to a method of use of the present compounds and other agents for the prevention and treatment of AIDS and viral infection by HIV.

DETAILED DESCRIPTION OF THE INVENTION

The present invention is directed to compounds of Formula I:

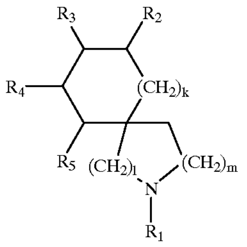

I wherein the nitrogen atom expressly shown above is optionally quaternized with $C_{1-4}$alkyl or phenyl$C_{1-4}$alkyl or is optionally present as the N-oxide ($N^+O^-$), and wherein:

k is 0, 1 or 2;

l and m are each independently 0, 1, 2, 3, 4, or 5, with the proviso that the sum of 1+m is equal to 1, 2, 3, 4, or 5;

$R_1$ is selected from a group consisting of:

(1) $C_{1-8}$ linear or branched alkyl, unsubstituted or mono, di, tri or tetra substituted, the substitutents independently selected from:
(a) hydroxy,
(b) oxo,
(c) cyano,
(d) halogen,
(e) trifluoromethyl,
(f) phenyl or naphthyl or mono, di or trisubstituted phenyl or naphthyl, the substitutents independently selected from:
(a) hydroxy,
(b) oxo,
(c) cyano,
(d) halogen,
(e) trifluoromethyl
(f) $—NR_6COR^7$,
(g) $—NR_6CO_2R^7$,
(h) $—NR_6CONHR^7$,
(i) $—NHS(O)_jR^6$,
(j) $—CONR^6R^7$,
(k) $—COR^6$,
(l) $—CO_2R^6$,
(m) $—OR^6$,
(n) $—S(O)_jR^6$,
(o) heteroaryl, wherein heteroaryl is as defined below, and
(p) phenyl;
(g) $—NR^6R^7$, wherein $R^6$ and $R^7$ are independently selected from:
(1) hydrogen,
(2) $C_{1-6}$ alkyl, or mono or disubstituted $C_{1-6}$ alkyl, the substitutents independently selected from
(a) hydroxy,
(b) oxo,
(c) cyano,
(d) halogen,
(e) trifluoromethyl
(f) $—NR^8COR^9$, wherein $R^8$ and $R^9$ selected from:
(1) hydrogen,
(2) $C_{1-6}$ alkyl, or mono or di-substituted $C_{1-6}$ alkyl, the substituents independently selected from:

(a) phenyl,
(b) hydroxy,
(c) oxo,
(d) cyano,
(e) halogen,
(f) trifluoromethyl, and
(3) phenyl or mono di or tri-substituted phenyl, the substituents independently selected from:
(a) hydroxy,
(b) $C_{1-3}$alkyl,
(c) cyano,
(d) halogen,
(e) trifluoromethyl;
(g) —$NR^8CO_2R^9$,
(h) —$NR^8CONHR^9$,
(i) —$NHS(O)_iR^8$,
(j) —$CONR^8R^9$,
(k) —$COR^8$,
(l) —$CO_2R^8$,
(m) —$OR^8$,
(n) —$S(O)_jR^8$,
(o) heteroaryl, wherein heteroaryl is as defined below, and
(p) phenyl;
(3) phenyl or mono di or trisubstituted phenyl, the substitutents independently selected from
(a) hydroxy,
(b) oxo,
(c) cyano,
(d) halogen,
(e) trifluoromethyl
(f) —$NR^8COR^9$,
(g) —$NR^8CO_2R^9$,
(h) —$NR^8CONHR^9$,
(i) —$NHS(O)_iR^8$,
(j) —$CONR^8R^9$,
(k) —$COR^8$,
(l) —$CO_2R^8$,
(m) —$OR^8$,
(n) —$S(O)_jR^8$,
(o) heteroaryl, wherein heteroaryl is as defined below, and
(p) phenyl;
or $R^6$ and $R_7$ are joined together to form a 5-, 6-, or 7-membered monocyclic saturated ring containing 1 or 2 heteroatoms independently selected from nitrogen, oxygen, and sulfur, and in which the ring is unsubstituted or mono or disubstituted, the substituents independently selected from
(a) hydroxy,
(b) oxo,
(c) cyano,
(d) halogen,
(e) trifluoromethyl
(f) —$NR^8COR^9$,
(g) —$NR^8CO_2R^9$,
(h) —$NR^8CONHR^9$,
(i) —$NHS(O)_iR^8$,
(j) —$CONR^8R^9$,
(k) —$COR^8$,
(l) —$CO_2R^8$,
(m) —$OR^8$,
(n) —$S(O)_jR^8$,
(o) heteroaryl, wherein heteroaryl is as defined below, and
(p) phenyl;
(h) —$NR^6COR^7$, (i) —$NR^6CO_2R^7$,
(j) —$NR^6CONHR^7$,
(k) —$NR^6S(O)_jR^7$, wherein j is 1 or 2,
(l) —$CONR^6R^7$,
(m) —$COR^6$,
(n) —$CO_2R^6$,
(o) —$OR^6$,
(p) —$S(O)_iR^6$, wherein i is 0, 1, or 2,
(q) —$NR^6$CO-heteroaryl,
(r) —$NR^6S(O)_j$-heteroaryl, and
(s) heteroaryl, wherein heteroaryl is selected from the group consisting of:
(1) benzimidazolyl,
(2) benzofuranyl,
(3) benzooxazolyl,
(4) furanyl,
(5) imidazolyl,
(6) indolyl,
(7) isooxazolyl,
(8) isothiazolyl,
(9) oxadiazolyl,
(10) oxazolyl,
(11) pyrazinyl,
(12) pyrazolyl,
(13) pyridyl,
(14) pyrimidyl,
(15) pyrrolyl,
(16) quinolyl,
(17) tetrazolyl,
(18) thiadiazolyl,
(19) thiazolyl,
(20) thienyl,
(21) triazolyl,
wherein the heteroaryl is unsubstituted or mono di or trisubstituted, the substituents independently selected from
(a) hydroxy,
(b) oxo,
(c) cyano,
(d) halogen,
(e) trifluoromethyl
(f) —$NR_6COR^7$,
(g) —$NR_6CO_2R^7$,
(h) —$NR_6CONHR^7$,
(i) —$NHS(O)_iR^6$,
(j) —$CONR^6R^7$,
(k) —$COR^6$,
(l) —$CO_2R^6$,
(m) —$OR^6$,
(n) —$S(O)_jR^6$, and
(o) phenyl;
(2) $C_{2-8}$ linear or branched alkenyl, unsubstituted or mono, di, tri or tetra substituted, the substitutents independently selected from:
(a) hydroxy,
(b) oxo,
(c) cyano,
(d) halogen,
(e) trifluoromethyl,
(f) phenyl, unsubstituted or mono or disubstituted, the substituents independently selected from
(a) hydroxy,
(b) oxo,
(c) cyano,
(d) halogen,
(e) trifluoromethyl
(f) —$NR_6COR^7$, (g) —$NR_6CO_2R^7$,
(h) —$NR_6CONHR^7$,
(i) —$NHS(O)_iR^6$,
(j) —$CONR^6R^7$,
(k) —$COR^6$,
(l) —$CO_2R^6$,
(m) —$OR^6$,
(n) —$S(O)_jR^6$,
(o) heteroaryl, wherein heteroaryl is as defined below, and
(p) phenyl;
(g) —$NR^6R^7$,
(h) —$NR^6COR^7$,
(i) —$NR^6CO_2R^7$,
(j) —$NR^6CONHR^7$,
(k) —$NR^6S(O)_jR^7$, wherein j is 1 or 2,
(l) —$CONR^6R^7$,
(m) —$COR^6$,
(n) —$CO_2R^6$,
(o) —$OR^6$,
(p) —$S(O)_iR^6$, wherein i is 0, 1, or 2,
(q) —$NR^6$CO-heteroaryl,
(r) —$NR^6S(O)_j$-heteroaryl, and
(s) heteroaryl, wherein heteroaryl is defined above;
(3) $C_{2-8}$ alkynyl, unsubstituted or mono, di tri or tetra substituted, the substitutents independently selected from;
(a) hydroxy,
(b) oxo,
(c) cyano,
(d) halogen,
(e) trifluoromethyl,
(f) phenyl, unsubstituted or mono or disubstituted, the substituents independently selected from
(a) hydroxy,
(b) oxo,
(c) cyano,
(d) halogen,
(e) trifluoromethyl
(f) —$NR_6COR^7$,
(g) —$NR_6CO_2R^7$,
(h) —$NR_6CONHR^7$,
(i) —$NHS(O)_iR^6$,
(j) —$CONR^6R^7$,
(k) —$COR^6$,
(l) —$CO_2R^6$,
(m) —$OR^6$,
(n) —$S(O)_jR^6$,
(o) heteroaryl, wherein heteroaryl is as defined below, and
(p) phenyl;
(g) —$NR^6R_7$,
(h) —$NR^6COR^7$,
(i) —$NR^6CO_2R^7$,
(j) —$NR^6CONHR^7$,
(k) —$NR^6S(O)_jR^7$, wherein j is 1 or 2,
(l) —$CONR^6R^7$,
(m) —$COR^6$,
(n) —$CO_2R^6$,
(o) —$OR^6$,
(p) —$S(O)_iR^6$, wherein i is 0, 1, or 2,
(q) —$NR^6$CO-heteroaryl,
(r) —$NR^6S(O)_j$-heteroaryl, and
(s) heteroaryl, wherein heteroaryl is defined above;

wherein the nitrogen of definitions —$NR^6R_7$ above is optionally quaternized with $C_{1-4}$alkyl or phenyl$C_{1-4}$alkyl or is optionally present as the N-oxide ($N^+O^-$);

$R^2$, $R^3$, $R^4$, and $R^5$ are independently selected from the group consisting of:
(1) hydrogen;
(2) hydroxy;
(3) oxo; and
(4) —$NR^6R^7$, wherein the nitrogen is optionally quaternized with $C_{1-4}$alkyl or phenyl$C_{1-4}$alkyl or is present as the N-oxide, or $R^2$ and $R^3$, or $R^3$ and $R^4$, together form a carbon-carbon bond, or $R^2$ and $R^3$, or $R^3$ and $R^4$, or $R^4$ and $R^5$ are joined to form an aryl or heteroaryl, wherein heteroaryl is as defined above and aryl is phenyl or napthyl, wherein the phenyl or napthyl is unsubstituted or mono di or trisubstituted, the substitutents independently selected from:
(a) $C_{1-6}$ linear or branched alkyl,
(b) $C_{2-6}$ linear or branched alkenyl,
(c) $C_{2-6}$ linear or branched alkynyl,
(d) cyano,
(e) halogen,
(f) trifluoromethyl,
(g) $C_{1-6}$ alkoxy,
(f) —$NR^6R^7$,
(g) —$NR^6COR^7$,
(h) —$NR_6CO_2R^7$,
(i) —$NR_6CONHR^7$,
(j) —$NR_6S(O)_j$—$R_7$
(k) —$CONR^6R^7$,
(l) —$COR^6$,
(m) —$CO_2R^6$,
(n) —$S(O)_iR6$;

X is carbon, or X—$R^5$ is oxygen or S—$(O)_i$; and pharmaceutically acceptable salts thereof.

In an alternative embodiment, the invention is directed to compounds of the Formula I:

I

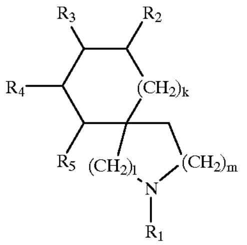

wherein the nitrogen atom expressly shown above is optionally quaternized with $C_{1-4}$alkyl or phenyl$C_{1-4}$alkyl or is optionally present as the N-oxide ($N^+O^-$), and wherein:

k is 0, 1 or 2;

l and m are each independently 0, 1, 2, 3, 4, or 5, with the proviso that the sum of 1+m is equal to 1, 2, 3, 4, or 5;

$R_1$ is selected from a group consisting of:
(1) hydrogen,
(2) linear or branched $C_{1-8}$ alkyl, linear or branched $C_{2-8}$ alkenyl, or linear or branched $C_{2-8}$ alkynyl, wherein the $C_{1-8}$ alkyl, $C_{2-8}$ alkenyl or $C_{2-8}$ alkynyl is optionally mono, di, tri or tetra substituted, the substitutents independently selected from:

(a) hydroxy,
(b) oxo,
(c) cyano,
(d) halogen, wherein halogen is selected from: Br, Cl, I, and F,
(e) trifluoromethyl,
(f) phenyl or naphthyl or mono, di or trisubstituted phenyl or naphthyl, the substituents independently selected from
(1') hydroxy,
(2') oxo,
(3') phenyl,
(4') $C_{1-3}$alkyl,
(5') cyano,
(6') halogen,
(7') trifluoromethyl,
(8') —$NR_6COR_7$, wherein $R_6$ and $R_7$ are independently selected from:
(a') hydrogen,
(b') $C_{1-6}$ alkyl, or mono or disubstituted $C_{1-6}$ alkyl, the substitutents independently selected from:
(1") phenyl,
(2") hydroxy,
(3") oxo,
(4") cyano,
(5") halogen,
(6") trifluoromethyl,
(c') phenyl or naphthyl or mono di or trisubstituted phenyl or naphthyl, the substitutents independently selected from:
(1") hydroxy,
(2") $C_{1-3}$alkyl,
(3") cyano,
(4") halogen,
(5") trifluoromethyl,
(d') $C_{1-3}$alkyloxy,
or $R_6$ and $R_7$ are joined together with the nitrogen to which they are attached to form a 5-, 6-, or 7-membered monocyclic saturated ring containing 1 or 2 heteroatoms independently selected from nitrogen, oxygen, and sulfur, and in which the ring is unsubstituted or mono or disubstituted, the substituents independently selected from
(1") hydroxy,
(2") oxo,
(3") cyano,
(4") halogen,
(5") trifluoromethyl,
(9') —$NR_6CO_2R_7$,
(10') —$NR_6CONHR_7$,
(11') —$NR_6S(O)_jR_7$, wherein j is 1 or 2,
(12') —$CONR_6R_7$,
(13') —$COR_6$,
(14') —$CO_2R_6$,
(15') —$OR_6$,
(16') —$S(O)_iR_6$, wherein i is 0, 1, or 2,
(17') heteroaryl, wherein heteroaryl is selected from the group consisting of:
(1") benzimidazolyl,
(2") benzofuranyl,
(3") benzooxazolyl,
(4") furanyl,
(5") imidazolyl,
(6") indolyl,
(7") isooxazolyl,
(8") isothiazolyl,
(9") oxadiazolyl,
(10") oxazolyl,
(11") pyrazinyl,
(12") pyrazolyl,
(13") pyridyl,
(14") pyrimidyl,
(15") pyrrolyl,
(16") quinolyl,
(17") tetrazolyl,
(18") thiadiazolyl,
(19") thiazolyl,
(20") thienyl, and
(21") triazolyl,
wherein the heteroaryl is unsubstituted or mono di or trisubstituted, the substituents independently selected from:
(a") hydroxy,
(b") oxo,
(c") cyano,
(d") halogen,
(e") trifluoromethyl,
(g) —$NR_6R_7$,
(h) —$NR_6COR_7$,
(i) —$NR_6CO_2R_7$,
(j) —$NR_6CONHR_7$,
(k) —$NR_6S(O)_jR_7$,
(l) —$CONR_6R_7$,
(m) —$COR_6$,
(n) —$CO_2R_6$,
(o) —$OR_6$,
(p) —$S(O)_iR_6$,
(q) heteroaryl, wherein heteroaryl is defined above;

wherein the nitrogen of definition —$NR_6R_7$ above is optionally quaternized with $C_{1-4}$alkyl or phenyl$C_{1-4}$alkyl or is optionally present as the N-oxide ($N^+O^-$);

$R^2$, $R^3$, $R^4$, and $R^5$ are independently selected from the group consisting of:
(1) hydrogen;
(2) hydroxy;
(3) oxo; and
(4) —$NR_6R_7$ or —$NR_6C(O)$—$NR_6R_7$, wherein the nitrogen of —$NR_6R_7$ is optionally quaternized with $C_{1-4}$alkyl or phenyl$C_{1-4}$alkyl or is optionally present as the N-oxide, or $R^2$ and $R^3$, or $R^3$ and $R^4$, together form a carbon-carbon bond, or $R^2$ and $R^3$, or $R^3$ and $R^4$, or $R^4$ and $R^5$ are joined to form a ring selected from the group consisting of:
(a) benzimidazolyl,
(b) benzofuranyl,
(c) benzooxazolyl,
(d) furanyl,
(e) imidazolyl,
(f) indolyl,
(g) isooxazolyl,
(h) isothiazolyl,
(i) naphthyl,
(j) oxadiazolyl,
(k) oxazolyl,
(l) phenyl
(m) pyrazinyl,
(n) pyrazolyl,
(o) pyridyl,
(p) pyrimidyl, (q) pyrrolyl, (r) quinolyl, (s) thiadiazolyl, (t) thiazolyl, (u) thienyl, and (v) triazolyl, and wherein the ring is unsubstituted, mono, di or tri substituted, the substitutents selected from:

(1') $C_{1-6}$ linear or branched alkyl, unsubstituted or mono or disubstituted, the substituents being selected from hydrogen and hydroxy, (2') $C_{2-6}$ linear or branched alkenyl, (3') hydroxy (4') oxo (5') —$OR_6$, (6') halogen, (7') trifluoromethyl, (8') nitro, (9') cyano, (10') —$NR^6R^7$, (11') —$NR^6COR^7$, (12') —$NR_6CO_2R^7$, (13') —$NR_6CONHR^7$, (14') —$NR_6S(O)_j$—$R_7$ (15') —$CONR^6R^7$, (16') —$COR^6$, (17') —$CO_2R^6$, (18') —$S(O)_jR_6$, and (19') heteroaryl, wherein heteroaryl is defined above;

X is carbon, or X—$R^5$ is oxygen or S—$(O)_i$; and pharmaceutically acceptable salts thereof.

Preferred compound for use in the present invention include those of Formula II:

II

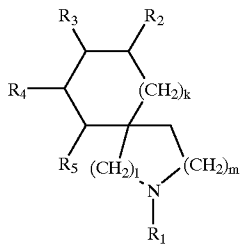

wherein k is 0 or 1;

the sum of l+m is 3;

$R_1$ is:

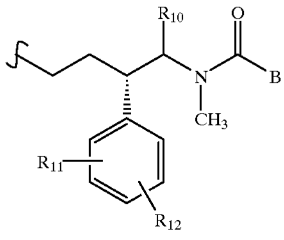

, or

-continued

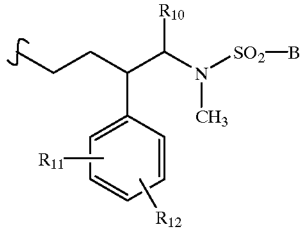

;

$R_2$ and $R_3$ are independently selected from: hydrogen, hydroxy, oxo, or —$NR_6C(O)R_7R_8$, wherein $R_6$, $R_7$ and $R_8$ are independently selected from:

(a) hydrogen, (b) $C_{1-6}$ alkyl, which is unsubstituted or mono or disubstituted, wherein the substitutents on alkyl are independently selected from: hydroxy, halo, trifluoromethyl, $C_{1-3}$alkyl, and phenyl;

(c) phenyl, unsubstituted or mono or disubstituted, the substitutents on phenyl are independently selected from: hydroxy, halo, trifluoromethyl, $C_{1-3}$alkyl and phenyl;

B is selected from:

(a) phenyl, naphthyl, mono di or trisubstituted phenyl, and mono di or trisubstituted naphthyl, wherein the substitutents on phenyl or naphthyl are independently selected from:

chloro, methyl, phenyl and $CF_3$;

(b) —$CH_2$-phenyl, or mono or disubstituted —$CH_2$-phenyl, wherein the substitutents on phenyl are independently selected from:

fluoro, chloro, methyl, phenyl or $CF_3$;

(c) pyridyl, or mono, di or trisubstituted pyridyl, wherein the substitutents on pyridyl are independently selected from:

chloro, methyl, phenyl or $CF_3$;

(d) thiophene, or mono or disubstituted thiophene, wherein the substitutents on thiophene are independently selected from:

chloro, methyl, phenyl or $CF_3$;

$R_4$ and $R_5$ are joined together to form a ring selected from: thiophene or substituted phenyl, wherein the substitutent on phenyl is selected from:

(a) hydrogen, (b) $CH_3O$—, (c) $CH_3SO_2NH$—, and (d) $CH_3SO_2$—;

$R_{10}$ is selected from: hydrogen, $C_{1-3}$alkyl, and phenyl;

$R_{11}$ and $R_{12}$ are independently selected from:

hydrogen, halogen, methyl, phenyl or $CF_3$;

and pharmaceutically acceptable salts thereof.

More preferred compounds for use in the present invention include the compounds of Formula II:

II

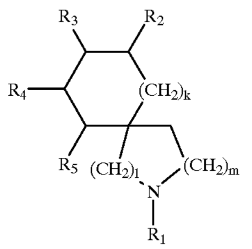

wherein:

k is 0 or 1;

the sum of l+m is 3;

$R_1$ is:

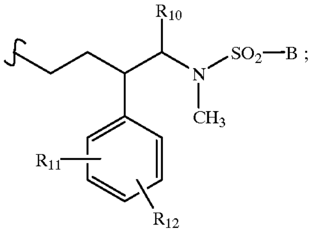

$R_2$ and $R_3$ are independently selected from:

hydrogen, hydroxy, oxo, and $—NR_6C(O)R_6R_7$;

B is selected from:

phenyl, mono or disubstituted phenyl, naphthyl, mono or disubstituted naphthyl, thiophene, and monosubstituted thiophene wherein the substitutent on phenyl, naphthyl or thiophene is selected from: $CF_3$, $CH_3$, Cl, F, and Br;

$R_4$ and $R_5$ are joined together to form a ring selected from:

thiophene and substituted phenyl, wherein the substitutent on phenyl is selected from:

(a) hydrogen, (b) $CH_3O—$, (c) $CH_3SO_2NH—$, and (d) $CH_3SO_2—$;

$R_{10}$ is hydrogen, $C_{1-3}$alkyl or phenyl;

$R_{11}$ and $R_{12}$ are independently selected from:

hydrogen, chloro, methyl, phenyl or $CF_3$;

and pharmaceutically acceptable salts thereof.

Even more preferred compounds for use in the present invention include those of Formula II wherein B is unsubstituted phenyl, 3-chlorophenyl, 3-fluorophenyl or unsubstituted thiophene.

Even more preferred compounds for use in the present invention include those of the Formula III:

III

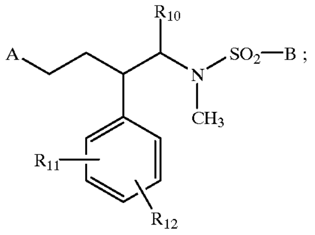

wherein A is selected from:

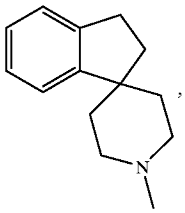
,
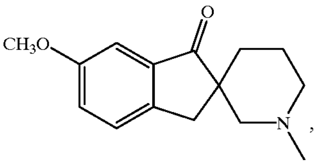
,
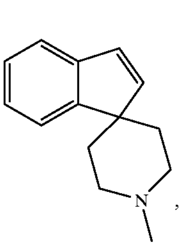
,
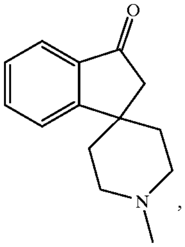
,
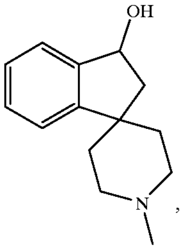
, and
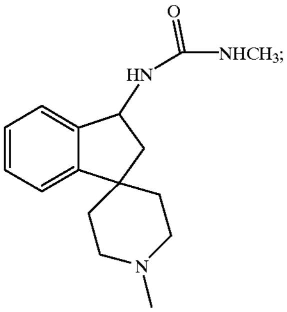

B is selected from:

phenyl, mono or disubstituted phenyl, thiophene, and monosubstituted thiophene wherein the substitutent on phenyl or thiophene is selected from:

$CF_3$, $CH_3$, Cl, F, and Br;

$R_{11}$ and $R_{12}$ are independently selected from:

hydrogen, chloro, methyl, phenyl or $CF_3$;

and pharmaceutically acceptable salts thereof.

Even more preferred compounds for use in the present invention include those of Formula III wherein B is unsubstituted phenyl, 3-chlorophenyl, 3-fluorophenyl or unsubstituted thiophene.

Even more preferred compounds for use in the present invention include those of Formula III wherein A is:

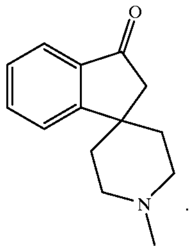

Even more preferred compounds for use in the present invention include those of Formula III wherein $R_{11}$ and $R_{12}$ are chloro.

Exemplifying the present invention is the use of a compound selected from the group consisting of:

1'-(3(S)-(3,4-dichlorophenyl)-4-(N-methyl)benzamidobutyl)spiro(1H-indene-1,4'-piperidine);

1'-(3(S)-(3,4-dichlorophenyl)-4-((N-methyl)-3,5-bis(trifluoromethyl)benzamidobutyl)spiro(1H-indene-1,4'-piperidine);

1'-((3S)-(3,4-dichlorophenyl)-4-(N-methyl)benzamidobutyl)-3,4-dihydro-4-hydroxy-6-methoxy-spiro[2H-1-benzopyran-2,3'-piperidine];

1'-((3S)-(3,4-dichlorophenyl)-4-(N-methyl)benzamidobutyl)-3,4-dihydro-4-hydroxy-6-methoxy-spiro[2H-1-benzopyran-2,4'-piperidine];

1'-((3S)-(3,4-dichlorophenyl)-4-(N-methyl)benzamidobutyl)spiro(indane-1,4'-piperidine);

1'-(1-oxo-(3S)-(3,4-dichlorophenyl)-4-(N-methyl)-benzamidobutyl)spiro(1H-indene-1,4'-piperidine);

1'-((3S)-(3,4-dichlorophenyl)-(4)-((N-methyl)benzamido)-pentyl)spiro(1H-indene-1,4'-piperidine);

1'-((2)-((3S)-(3,4-dichlorophenyl)-5-(N-methyl)-benzamido)pentyl)spiro(1-indane-1,4'-piperidine);

1'-((3S)-(3,4-dichlorophenyl)-(4)-((N-methyl)benzamido)octyl)spiro(1H-indene-1,4'-piperidine);

1'-((4)-((3S)-(3,4-dichlorophenyl)-1-(N-methyl)-benzamido)octyl)spiro(1H-indene-1,4'-piperidine);

1'-((3S)-(3,4-dichlorophenyl)-4-((N-methyl)benzenesulfonamidobutyl) spiro[1H-indene-1,4'-piperidine];

1'-((3S)-(3,4-dichlorophenyl)-4-((N-methyl)furan-2-carboxamidobutyl) spiro[1H-indene-1,4'-piperidine];

1'-((3S)-(3,4-dichlorophenyl)-4-((N-methyl)phenoxycarboxamidobutyl)spiro[1H-indene-1,4'-piperidine];

1'-((3S)-(3,4-dichlorophenyl)-4-((N-methyl)phenylaminocarboxamidobutyl)spiro[1H-indene-1,4'-piperidine];

1'-((3S)-(3,4-dichlorophenyl)-4-((N-methyl)pyridine-2-carboxamidobutyl)spiro[1H-indene-1,4'-piperidine];

1'-((3S)-(3,4-dichlorophenyl)-4-((N-methyl)pyridine-3-carboxamidobutyl)spiro[1H-indene-1,4'-piperidine];

1'-((3S)-(3,4-dichlorophenyl)-4-((N-methyl)pyridine-4-carboxamidobutyl)spiro[1H-indene-1,4'-piperidine];

1'-((3S)-(3,4-dichlorophenyl)-4-((N-methyl)benzothiophene-2-carboxamidobutyl)spiro[1H-indene-1,4'-piperidine];

1'-((3S)-(3,4-dichlorophenyl)-4-((N-methyl)thiophene-2-acetamidobutyl)spiro[1H-indene-1,4'-piperidine];

1'-((3S)-(3,4-dichlorophenyl)-4-((N-methyl)thiophene-3-carboxamidobutyl)spiro[1H-indene-1,4'-piperidine];

1'-((3S)-(3,4-dichlorophenyl)-4-((N-methyl)-(3-methylthiophene-2-carboxamido)butyl)spiro[1H-indene-1,4'-piperidine];

1'-((3S)-(3,4-dichlorophenyl)-4-((N-methyl)-(5-methylthiophene-2-carboxamido)butyl)spiro[1H-indene-1,4'-piperidine];

1'-((3S)-(3,4-dichlorophenyl)-4-((N-methyl)-(5-chlorothiophene-2-carboxamido)butyl)spiro[1H-indene-1,4'-piperidine];

1'-((3S)-(3,4-dichlorophenyl)-4-((N-methyl)-(2,3-dibromo-thiophene-5-carboxamido)butyl)spiro[1H-indene-1,4'-piperidine];

1'-[3-(S)-(3,4-dichlorophenyl)-4-(t-butoxycarbonyl(methyl-amino))butyl]-spiro(1H-indene-1,4'-piperidine);

1'-[3-(S)-(3,4-dichlorophenyl)-4-(N-(3,5-dichloro)benzoyl-(methylamino))butyl]-spiro(1H-indene-1,4'-piperidine);

1'-[3-(S)-(3,4-dichlorophenyl)-4-(N-(3-chloro)benzoyl-(methylamino))butyl]-spiro(1H-indene-1,4'-piperidine);

1'-[3-(S)-(3,4-dichlorophenyl)-4-(N-(3-trifluoromethyl)-benzoyl-(methylamino))butyl]-spiro(1H-indene-1,4'-piperidine);

1'-[3-(S)-(3,4-dichlorophenyl)-4-(N-(3-isopropyloxy)-benzoyl-(methylamino))butyl]-spiro(1H-indene-1,4'-piperidine);

1'-[3-(S)-(3,4-dichlorophenyl)-4-(N-(3-isopropyloxy)-phenylacetyl-(methylamino))butyl]-spiro(1H-indene-1,4'-piperidine);

1'-[3-(S)-(3,4-dichlorophenyl)-4-(N-(4-t-butyl)benzoyl-(methylamino))butyl]-spiro(1H-indene-1,4'-piperidine;

1'-[3-(S)-(3,4-dichlorophenyl)-4-(N-(2-phenyl)benzoyl-(methylamino))butyl]-spiro(1H-indene-1,4'-piperidine);

1'-[3-(S)-(3,4-dichlorophenyl)-4-(N-(1-naphthoyl-(methylamino))butyl]-spiro(1H-indene-1,4'-piperidine);

1'-[3-(S)-(3,4-dichlorophenyl)-4-(N-(2-naphthoyl-(methylamino))butyl]-spiro(1H-indene-1,4'-piperidine);

1'-[3-(S)-(3,4-dichlorophenyl)-4-(N-(2-methyl)benzoyl-(methylamino))butyl]-spiro(1H-indene-1,4'-piperidine);

1'-[3-(S)-(3,4-dichlorophenyl)-4-(N-(4-methyl)benzoyl-(methylamino))butyl]-spiro(1H-indene-1,4'-piperidine);

1'-[3-(S)-(3,4-dichlorophenyl)-4-(N-(3-methyl)benzoyl-(methylamino))butyl]-spiro(1H-indene-1,4'-piperidine);

1'-[3-(S)-(3,4-dichlorophenyl)-4-(N-(3,5-dimethyl)benzoyl-(methylamino))butyl]-spiro(1H-indene-1,4'-piperidine);

1'-[3-(S)-(3,4-dichlorophenyl)-4-(N-(2,3-dimethyl)benzoyl-(methylamino))butyl]-spiro(1H-indene-1,4'-piperidine);

1'-[3-(S)-(3,4-dichlorophenyl)-4-(N-(3,4-dimethyl)benzoyl-(methylamino))butyl]-spiro(1H-indene-1,4'-piperidine);

1'-[3-(S)-(3,4-dichlorophenyl)-4-(N-(2,5-dimethyl)benzoyl-(methylamino))butyl]-spiro(1H-indene-1,4'-piperidine);

1'-[3-(S)-(3,4-dichlorophenyl)-4-(N-(2,4-dimethyl)benzoyl-(methylamino))butyl]-spiro(1H-indene-1,4'-piperidine);

1'-[3-(S)-(3,4-dichlorophenyl)-4-(trifluoroacetyl-(methylamino))butyl]-spiro(1H-indene-1,4'-piperidine);

1'-[3-(S)-(3,4-dichlorophenyl)-4-(t-butylcarbonyl-(methylamino))butyl]-spiro(1H-indene-1,4'-piperidine);

1'-[3-(S)-(3,4-dichlorophenyl)-4-(1-adamentanecarbonyl-(methylamino))butyl]-spiro(1H-indene-1,4'-piperidine);

1'-[3-(S)-(3,4-dichlorophenyl)-4-(cyclohexanecarbonyl-(methylamino))butyl]-spiro(1H-indene-1,4'-piperidine);

1'-[3-(S)-(3,4-dichlorophenyl)-4-(N-(3-methyl)benzoyl-(methylamino))butyl]-spiro[indane-1,4'-piperidine];

1'-[3-(S)-(3,4-dichlorophenyl)-4-(N-(3,5-dimethyl)benzoyl-(methylamino))butyl]-spiro[indane-1,4'-piperidine];

1'-[3-(S)-(3,4-dichlorophenyl)-4-(N-(3,5-bistrifluoromethyl)benzoyl-(methylamino))butyl]-spiro[(3-indanone)-1,4'-piperidine];

1'-[3-(S)-(3,4-dichlorophenyl)-4-(N-benzoyl-(methylamino))butyl]-spiro[(3-indanone)-1,4'-piperidine];

1'-[3-(S)-(3,4-dichlorophenyl)-4-(N-(3,5-dimethyl)benzoyl-(methylamino))butyl]-spiro[(3-indanone)-1,4'-piperidine];

1'-[3-(S)-(3,4-dichlorophenyl)-4-(t-butoxycarbonyl-(methylamino))butyl]-spiro[(3-indanone)-1,4'-piperidine];

1'-[3-(S)-(3,4-dichlorophenyl)-4-(N-(3,5-dichloro)benzoyl-(methylamino))butyl]-spiro[(3-indanone)-1,4'-piperidine];

1'-[3-(S)-(3,4-dichlorophenyl)-4-(N-(3-chloro-5-methyl)-benzoyl(methylamino))butyl]-spiro[(3-indanone)-1,4'-piperidine];

1'-[3-(S)-(3,4-dichlorophenyl)-4-(N-(3-fluoro-5-methyl)-benzoyl-(methylamino))butyl]-spiro[(3-indanone)-1,4'-piperidine];

1'-[3-(S)-(3,4-dichlorophenyl)-4-(1-naphthoyl(methylamino))butyl]-spiro[(3-indanone)-1,4'-piperidine];

1'-[3-(S)-(3,4-dichlorophenyl)-4-(N-(3,5-dimethyl)benzoyl-(methylamino))butyl]-spiro[(3-hydroxy)indane)-1,4'-piperidine];

1'-[3-(S)-(3,4-dichlorophenyl)-4-(N-(3,5-dimethyl)benzoyl-(methylamino))butyl]-spiro[(3-acetyloxy)indane)-1,4'-piperidine];

1'-[3-(S)-(3,4-dichlorophenyl)-4-(N-(3,5-dimethyl)benzoyl-(methylamino))butyl]-spiro[(3-methylamino-carbonyl-amino)indane-1,4'-piperidine];

1'-[3-(S)-(3,4-dichlorophenyl)-4-(N-(3,5-bistrifluoromethyl)benzoyl-(methylamino))butyl]-spiro[(3-ethoxycarbonyl)indane)-1,4'-piperidine];

1'-[3-(S)-(3,4-dichlorophenyl)-4-(benzoyl(methylamino))-butyl]-spiro[(3-ethoxycarbonyl)indane)-1,4'-piperidine];

1'-(3-((S)-(3-chlorophenyl))-4-(N-(phenylsulfonyl)(methyl-amino))-butyl)-spiro(indan-1-one-3,4'-piperidine);

1'-(3-((S)-(3-chlorophenyl))-4-(N-(phenylsulfonyl)(methyl-amino))-butyl)-spiro(1-hydroxyindane-3,4'-piperidine);

1'-(3-((S)-(3-Chlorophenyl))-4-(N-(phenylsulfonyl)(methyl-amino))-butyl)-spiro(indane-1,4'-piperidine); and 1'-(3-((S)-(3-Chlorophenyl))-4-(N-(phenylsulfonyl)(methyl-amino))-butyl)-spiro(6-methoxyindan-1-one-2,4'-piperidine);

and pharmaceutically acceptable salts thereof.

The subject compounds are useful in a method of modulating chemokine receptor activity in a patient in need of such modulation comprising the administration of an effective amount of the compound.

As is clear from the examples and schemes, the designation:

 or  or 

in formula I is interchangable with $(CH_2)_k$ or $(CH_2)_l$ or $(CH_2)_m$ respectively. As appreciated by those of skill in the art, halo as used herein are intended to include chloro, fluoro, bromo and iodo.

The present invention is directed to the use of the foregoing spiro-substituted azacycles as modulators of chemokine receptor activity. In particular, these compounds are useful as modulators of the chemokine receptors, including CCR-1, CCR-2, CCR-2A, CCR-2B, CCR-3, CCR-4, CCR-5, CXCR-3, and/or CXCR-4.

The present invention is further directed to the use of compounds of this general structure which are disclosed as being antagonists of neurokinin receptors. Such compounds are disclosed, for example, in: U.S. Pat. Nos. 5,317,020; 5,534,525; 5,350,852; 5,411,971; 5,446,052; 5,560,700; EP 0 559 538, Sep. 8, 1993; EP 0 591 040, Apr. 6, 1994; EP 0 698 601, Feb. 28, 1996; EP 0 625 509, Nov. 23, 1994; EP 0 630 887, Dec. 28, 1994; EP 0 680 962, Nov. 8, 1995; EP 0 709 375, May 1, 1996; EP 0 709 376, May 1, 1996; EP 0 723 959, Jul. 31, 1996; EP 0 739 891; WO 94/10146, May 11, 1994; WO 94/17045, Aug. 4, 1994; WO 94/26735, Nov.24, 1994; WO 94/29309, Dec.22, 1994; WO 95/05377, Feb. 23, 1995; WO 95/12577, May 11, 1995; WO 95/15961, Jun. 15, 1995; WO 95/16682, Jun. 22, 1995; WO 95/21187; WO 95/26335, Oct. 5, 1995; WO 95/26338, Oct. 5, 1995; WO 95/35279; WO 96/06094, Feb. 29, 1996; WO 96/10568, Apr.11, 1996; WO 96/23787, Aug. 8, 1996; WO 96/24582, Aug.15, 1996; WO 96/28441; and WO 96/32385. Accordingly, the present invention embraces the use of a compound disclosed in these publications as a modulator of chemokine receptor activity.

The utility of the compounds in accordance with the present invention as modulators of chemokine receptor activity may be demonstrated by methodology known in the art, such as the assay for CCR-1 and/or CCR-5 binding as disclosed by Van Riper, et al., *J. Exp. Med.*, 177, 851–856 (1993), and the assay for CCR-2 and/or CCR-3 binding as disclosed by Daugherty, et al., *J. Exp. Med.*, 183, 2349–2354 (1996). Cell lines for expressing the receptor of interest include those naturally expressing the receptor, such as EOL-3 or THP-1, or a cell engineered to express a recombinant receptor, such as CHO, RBL-2H3, HEK-293. For example, a CCR3 transfected AML14.3D10 cell line has been placed on restricted deposit with American Type Culture Collection in Rockville, Md. as ATCC No. CRL-12079, on Apr. 5, 1996. The utility of the compounds in accordance with the present invention as inhibitors of the spread of HIV infection in cells may be demonstrated by methodology known in the art, such as the HIV quantitation assay disclosed by Nunberg, et al., *J. Virology*, 65 (9), 4887–4892 (1991).

In particular, the compounds of the following examples had activity in binding to either the CCR-5 receptor or the CCR-3 receptor in the aforementioned assays. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, including asthma and allergic diseases, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migrans (e.g., Toxocara), eosinophilic gastroenteritis (e.g., Anisaki spp., Phocanema ssp.), cutaneous larva migrans (*Ancylostona brazzliense, Ancylostoma caninum*).

The compounds of the present invention are accordingly useful in the prevention and treatment of a wide variety of inflammatory and immunoregulatory disorders and diseases.

In another aspect, the instant invention may be used to evaluate putative specific agonists or antagonists of chemokine receptors, including CCR-1, CCR-2, CCR-2A, CCR-2B, CCR-3, CCR-4, CCR-5, CXCR-3, and CXCR-4. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-1, CCR-2, CCR-2A, CCR-2B, CCR-3, CCR-4, CCR-5, CXCR-3, and CXCR-4. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery. In addition, a compound of the present invention may be used for the prevention of infection by HIV and the prevention of AIDS, such as in post-coital prophylaxis or in the prevention of maternal transmission of the HIV virus to a fetus or a child upon birth.

In a preferred aspect of the present invention, a subject compound may be used in a method of inhibiting the binding of a human immunodeficiency virus to a chemokine receptor, such as CCR-5 and/or CXCR-4, of a target cell, which comprises contacting the target cell with an amount of the compound which is effective at inhibiting the binding of the virus to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism and/or partial agonism. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; an antiitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the pressent invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3 and CCR-5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

| Drug Name | Manufacturer | Indication |
|---|---|---|
| 097 | Hoechst/Bayer | HIV infection, AIDS, ARC (non-nucleoside reverse transcriptase (RT) inhibitor) |
| 141 W94 | Glaxo Wellcome | HIV infection, AIDS, ARC (protease inhibitor) |
| 1592U89 | Glaxo Wellcome | HIV infection, AIDS, ARC (protease inhibitor) |
| Abacavir (1592U89) | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |

-continued

| Drug Name | Manufacturer | Indication |
|---|---|---|
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| (−)6-Chloro-4(S)-cyclopropylethynyl-4(S)-trifluoro-methyl-1,4-dihydro-2H-3,1-benzoxazin-2-one | Merck | HIV infection, AIDS, ARC (non-nucleoside reverse transcriptase inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-266 | DuPont-Merck Pharmaceuticals | HIV infection, AIDS, ARC (non-nucleoside reverse transcriptase inhibitor) |
| DMP-450 | AVID (Camden, NJ) | HIV infection, AIDS, ARC (protease inhibitor) |
| Efavirenz (DMP 266) | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| GW 141 | Glaxo Welcome | HIV infection, AIDS, ARC (protease inhibitor) |
| GW 1592 | Glaxo Welcome | HIV infection, AIDS, ARC |

-continued

| Drug Name | Manufacturer | Indication |
|---|---|---|
| | | (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma, in combination with other therapies |

IMMUNO-MODULATORS

| Drug Name | Manufacturer | Indication |
|---|---|---|
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

ANTI-INFECTIVES

| Drug Name | Manufacturer | Indication |
|---|---|---|
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |

OTHER

| Drug Name | Manufacturer | Indication |
|---|---|---|
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Megestrol Acetate | Bristol-Myers Squibb | treatment of anorexia assoc. w/AIDS |
| Testosterone | Alza, Smith Kline | AIDS-related wasting |
| Total Enteral Nutrition | Norwich Eaton Pharmaceuticals | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanoiate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of The present invention are employed. (For purposes of this application, topical application shall include mouth washes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples.

The compounds of the present invention are prepared by alkylating azacycle I, in which $R_1$=H, under appropriate conditions (Scheme 1). The required azacycle starting materials are prepared using methods described in the literature; more specifically, as described in Claremon, D. A. et al, European Patent 0 431 943 943 A2, Evans, B. E. et al, U.S. Pat. No. 5,091,387, Davis, L. et al, U.S. Pat. No. 4,420,485, all of which are incorporated by reference, and Parham et al, *Journal of Organic Chemistry*, 41, 2628 (1976).

Thus, azacycle I ($R_1$=H) is combined with the appropriate aldehyde and the intermediate imine is reduced to the tertiary amine chemically (e.g. using sodium cyanoborohydride) or catalytically (e.g. using hydrogen and palladium on carbon or Raney nickel catalyst) (Scheme 1). The aldehyde needed for this reaction can be prepared by methods generally known in the chemical literature; for the purposes of the present invention the preparation of a representative aldehyde is described in Hale, J. J.; Finke, P. E.; MacCoss, M. *Bioorganic and Medicinal Chemistry Letters*, 2, (February 1993).

In an alternative embodiment of the present invention, azacycle I ($R_1$=H) can be alkylated with an alkyl halide or alkyl sulfonate ester (with or without an added base to neutralize the mineral acid or sulfonic acid by-product) to give the desired compound (Scheme 1). The alkyl halide or alkyl sulfonate needed for this reaction can be prepared by methods generally known in the chemical literature; for the purposes of the present invention an aldehyde, prepared as described above, can be reduced to an alcohol with sodium borohydride, diisobutylaluminum hydride or lithium aluminum hydride, and the product alcohol converted to either the alkyl halide using methods described in March J. "Advanced Organic Chemistry", 3rd ed., John Wiley Sons, New York, pp. 382–384 (1985), or alkyl sulfonate ester using methods described in March J. "Advanced Organic Chemistry", 3rd ed., John Wiley Sons, New York, p. 444 (1985).

In an alternative embodiment of the present invention, I ($R_1$=H) can be acylated to give the tertiary amide and subsequent reduction with a strong reducing agent (e.g. diborane including borane dimethylsulfide; and, lithium aluminum hydride) will give the desired compound (Scheme 1). The acylating agent needed for this reaction can be prepared by methods generally known in the chemical literature; for the purposes of the present invention an aldehyde, prepared as described above, can be oxidized using such commonly used reagents as permanganate in acid or silver oxide, and the resulting acid activated as an acid chloride or mixed anhydride which can be used to acylate I ($R_1$=H). The product amide can be reduced with a strong reducing agent, such as diborane of lithium aluminum hydride, to give the tertiary amine.

Scheme 1

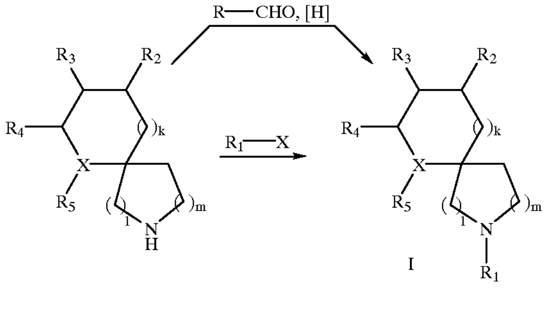

-continued

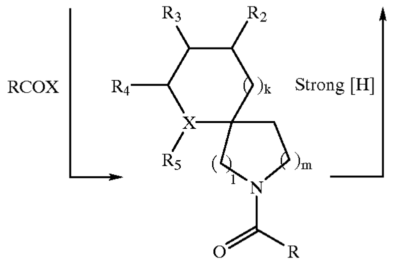

wherein $R_1$ as defined in this specification is R—$CH_2$.

The following examples are provided for the purpose of further illustration only and are not intended to be limitations on the disclosed invention.

EXAMPLE 1

1'-(3-(S)-(3,4-Dichlorophenyl)-4-(N-methyl)benzamidobutyl)spiro(1H-indene-1,4'-piperidine)

A mixture of 125 mg (0.36 mmol) of (3S)-(3,4-dichlorophenyl)-4-(N-methyl)benzamidobutanal, 107 mg (0.48 mmol) of spiro(1H-indene-1,4'-piperidine) hydrochloride, and 100 mg of activated 3 Å molecular sieves in 2 mL of methanol was treated with 1.5 mL of 1.0 M sodium cyanoborohydride solution in THF and stirred at room temperature for 20 hours. The mixture was filtered through a pad of Celite; the reaction flask and filtered solids were rinsed well with methanol (~25 mL). Saturated sodium bicarbonate solution (5 mL) was added to the filtrate and the resulting milky mixture was concentrated in vacuo. The residue was partitioned between 25 mL of ethyl acetate and 10 mL of water and the layers were separated. The organic layer was dried over magnesium sulfate and concentrated in vacuo. Flash chromatography on 8 g of silica gel using ether, then 20:1 v/v ether/methanol as the eluant afforded 146 mg (78%) of the title compound as a foam. $^1$H NMR ($CDCl_3$, 400 MHz, ppm, ranges are given due to amide rotamers and line broadening): δ 0.80–4.05 ppm (18 H), 6.75 (app s, 1 H), 6.79 (app s, 1 H), 6.95–7.50 (12 H). 2.69 and 3.04 (—$CH_2$N(<u>$CH_3$</u>)COPh). Mass Spectrum (FAB): 521 (M+H, $^{37}$Cl+$^{35}$Cl isotope), 519 (M+H, $^{35}$Cl+$^{35}$Cl isotope).

The following table summarizes compounds that were prepared using a procedure analogous to Example 1 substituting the required spiroazacycle hydrochloride for the spiro(1H-indene-1,4'-piperidine) hydrochloride. Methylene chloride/methanol/ammonium hydroxide (40:1:0.1 v/v/v) was used as the chromatography eluant.

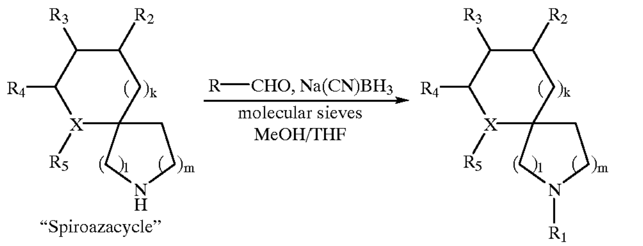

"Spiroazacycle"

| EXAMPLE | "Spiroazacycle" | $R_1$ |
|---|---|---|
| 2 | 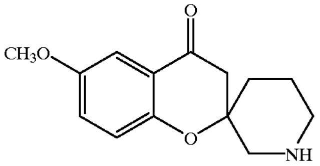 | 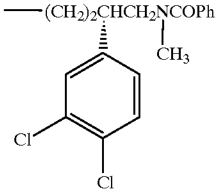 |

$^1H$ NMR ($CDCl_3$, 400 MHz, ppm): δ 1.50–3.75 (20 H), 3.77 (s, 3 H), 6.62–7.43 (11 H). Mass Spectrum (FAB): 583 (M+H, $^{37}Cl+^{35}Cl$ isotope), 581 (M+H, $^{35}Cl+^{35}Cl$ isotope).

3

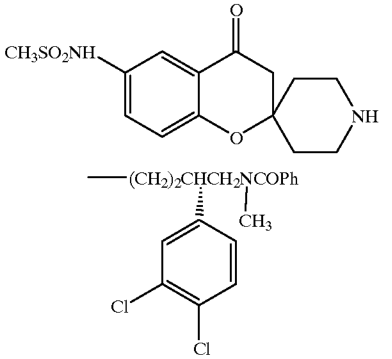

$^1H$ NMR ($CDCl_3$, 400 MHz, ppm): δ 1.58–3.95 (24 H), 6.72–7.62 (11 H). Mass Spectrum (FAB): 646 (M+H, $^{37}Cl+^{35}Cl$ isotope), 644 (M+H, $^{35}Cl+^{35}Cl$ isotope).

5

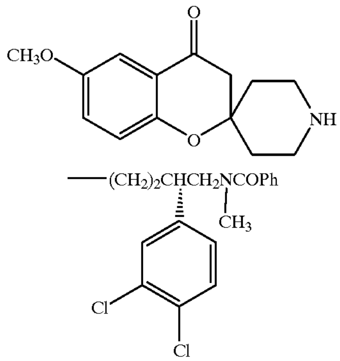

$^1H$ NMR ($CDCl_3$, 400 MHz, ppm): δ 1.56–3.57 (20 H), 3.90 (m, 1 H), 6.72–7.43 (11 H), 3.77 (<u>$CH_3$</u>O—) Mass Spectrum (FAB): 583 (M+H, $^{37}Cl+^{35}Cl$ isotope), 581 (M+H, $^{35}Cl+^{35}Cl$ isotope).

| EXAMPLE | "Spiroazacycle" | $R_1$ |
|---|---|---|
| 4 | 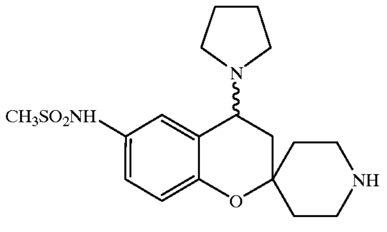 | 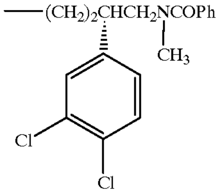 |

$^1H$ NMR ($CDCl_3$, 400 MHz, ppm): δ 1.70–4.18 (33 H), 6.72–7.47 (11 H). Mass Spectrum (FAB): 701 (M+H, $^{37}Cl+^{35}Cl$isotope), 699 (M+H, $^{35}Cl+^{35}Cl$ isotope).

| EXAMPLE | "Spiroazacycle" | $R_1$ |
|---|---|---|
| 6 | 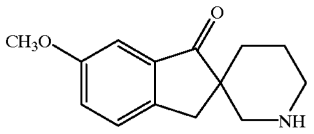 | 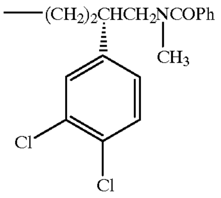 |

$^1$H NMR ($CDCl_3$, 400 MHz, ppm): δ 1.39–3.50 (20 H), 6.70–7.40 (11 H). 3.80 ($\underline{CH_3}O$—) Mass Spectrum (FAB): 567 (M+H, $^{37}Cl+^{35}Cl$ isotope), 565 (M+H, $^{35}Cl+^{35}Cl$ isotope).

7

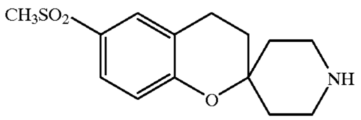

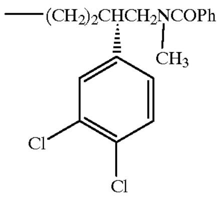

$^1$H NMR ($CDCl_3$, 400 MHz, ppm): δ 1.45–3.97 (25 H), 6.73–7.65 (11 H). Mass Spectrum (FAB): 617 (M+H, $^{37}Cl+^{35}Cl$ isotope), 615 (M+H, $^{35}Cl+^{35}Cl$ isotope).

| EXAMPLE | "Spiroazacycle" | $R_1$ |
|---|---|---|
| 8 | 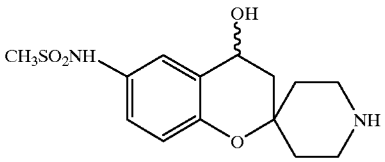 | 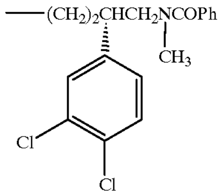 |

$^1$H NMR ($CDCl_3$, 400 MHz, ppm): δ 1.65–3.60 (24 H), 3.95 (m, 1 H), 4.75 (m, 1 H), 6.70–7.40 (11 H). Mass Spectrum (FAB): 648 (M+H, $^{37}Cl+^{35}Cl$ isotope) 646 (M+H, $^{35}Cl+^{35}Cl$ isotope).

9

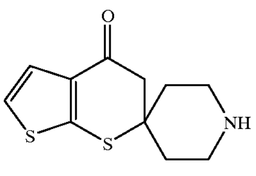

-continued

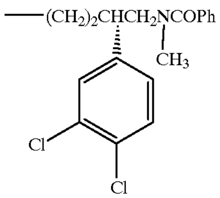

$^1$H NMR ($CDCl_3$, 400 MHz, ppm): δ 1.40–3.95 (16 H), 6.70–7.45 (8 H), 7.00 (app s, 1 H), 7.03 (app s, 1 H), 2.67 and 2.81 (—$CH_2N(\underline{CH_3})COPh$) Mass Spectrum (FAB): 575 (M+H, $^{37}Cl+^{35}Cl$ isotope), 573 (M+H, $^{35}Cl+^{35}Cl$ isotope).

| EXAMPLE | "Spiroazacycle" | $R_1$ |
|---|---|---|
| 10 | 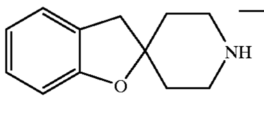 | 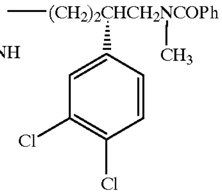 |

$^1$H NMR ($CDCl_3$, 400 MHz, ppm): δ 1.45–3.95 (17 H), 6.70–7.45 (12 H) 2.69 and 2.97 (—$CH_2N(\underline{CH_3})COPh$) Mass Spectrum (FAB): 525 (M+H, $^{37}Cl+^{35}Cl$ isotope), 523 (M+H, $^{35}Cl+^{35}Cl$ isotope).

11

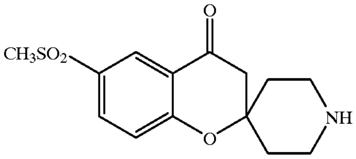

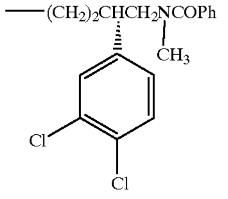

$^1H$ NMR ($CDCl_3$, 400 MHz, ppm): δ 1.60–3.95 (23 H), 6.70–7.42 (9 H), 7.98 (dd, 1 H, J=2.4, 8.7), 8.41 (d, 1 H, J=2.32). Mass Spectrum (FAB): 631 (M+H, $^{37}Cl$+$^{35}Cl$ isotope), 629 (M+H, $^{35}Cl$+$^{35}Cl$ isotope).

| EXAMPLE | "Spiroazacyle" | $R_1$ |
|---|---|---|
| 12 | 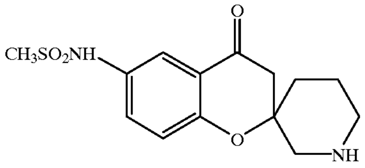 | 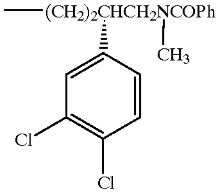 |

$^1H$ NMR ($CDCl_3$, 400 MHz, ppm): δ 1.15–4.00 (24 H), 6.65–7.77 (11 H). Mass Spectrum (FAB): 645 (M+H, $^{37}Cl$+$^{35}Cl$ isotope), 643 (M+H, $^{35}Cl$+$^{35}Cl$ isotope).

EXAMPLE 13

1'-(3-(S)-(3,4-Dichlorophenyl)-4-((N-methyl)-3,5-bis (trifluoromethyl)-benzamidobutyl)spiro(1H-indene-1,4'-piperidine)

STEP 1: N-Methyl-N-((2S)-(3,4-dichlorophenyl)-4-pentenyl)-3,5-bis(trifluoromethyl) benzamide.

A rapidly stirred mixture of 135 mg (0.55 mmol) of N-methyl (2S)-(3,4-dichlorophenyl)-4-pentenamine, 2 mL of saturated aqueous sodium bicarbonate solution and 4 mL of toluene was treated with 0.35 mL (1.9 mmol) of 3,5-bis (trifluoromethyl) benzoyl chloride and the resulting mixture was stirred at room temperature for 20 minutes. The reaction mixture was diluted with 25 mL of ether and the layers were separated. The organic layer was washed with 10 mL of 2.0 N sodium hydroxide solution, 10 mL of 2.0 N hydrochloric acid solution, 10 mL of saturated aqueous sodium chloride solution, dried over magnesium sulfate and concentrated in vacuo. Flash chromatography on 12 g of silica gel using 4:1 v/v hexanes/ether as the eluant afforded 263 mg (99%) of the title compound as an oil, [α]D=−27.6 (c=0.5, $CHCl_3$, 20° C.). $^1H$ NMR (CDC13, 400 MHz, ppm, ranges are given due to amide rotamers and line broadening): δ 2.15–3.85 (5 H), 2.71 and 3.07 (3 H, $—CH_2N(\underline{CH_3})COAr$), 4.95–5.07 (2 H, $—CH_2CH{=}\underline{CH_2}$), 5.40–5.75 (1 H, $—CH_2\underline{CH}{=}CH_2$), 6.70–8.50 (6 H).

IR (neat): 1726, 1643, 1470, 1371, 1228, 1122,993, 905, 681.

Mass Spectrum (FAB): 486 ($^{37}Cl$+$^{35}Cl$ isotope), 484 ($^{35}Cl$+$^{35}Cl$ isotope).

Analysis: Calculated for $C_{21}H_{17}Cl_2F_6NO$ C, 52.08; H, 3.54; N, 2.89

Found: C, 51.13; H, 3.31; N, 2.45.

STEP 2: 1'-(3-(S)-(3,4-Dichlorophenyl)-4-((N-methyl)-3,5-bis(trifluoromethyl) benzamidobutyl)spiro(1H-indene-1,4'-piperidine).

A solution of 250 mg (0.52 mmol) of N-methyl-N-((2S)-(3,4-dichlorophenyl)-4-pentenyl)-3,5-bis(trifluoromethyl) benzamide (EXAMPLE 13, STEP 1) in 8 mL of 2:1:1 v/v/v acetone/t-butanol/water was treated with 5 mg (0.02 mmol) of osmium tetroxide. After 5 min, 91 mg (0.77 mmol) of N-methylmorpholine N-oxide was added and the resulting mixture was stirred at room temperature for 1.5 h. The reaction was quenched with approximately 100 mg of sodium bisulfite and concentrated in vacuo to 25% of the original volume. The residue was partitioned between 50 mL of methylene chloride and 20 mL of water and the layers were separated. The organic layer was dried over magnesium sulfate. The aqueous layer was extracted with 25 mL of methylene chloride; the extract was dried and combined with the original organic layer. The combined organic layers were concentrated in vacuo to afford the crude diol.

A solution of the diol in 8 mL of 3:1 v/v THF/water was treated with 197 mg (0.92 mmol) of sodium periodate. After 30 min, the reaction mixture was partitioned between 50 mL of ether and 25 mL of water and the layers were separated. The organic layer was dried. The aqueous layer was extracted with 50 mL of ether; the extract was dried and combined with the original organic layer. The combined organic layers were concentrated in vacuo. The residue was filtered through a pad of 10 g of silica gel using 3:2 v/v ether/hexanes as the eluant to afford 154 mg (61%) of aldehyde.

A solution of 150 mg (0.31 mmol) of aldehyde and 115 mg (0.52 mmol) of spiro(1H-indene-1,4'-piperidine) hydrochloride in 3 mL of methanol was treated with 1.5 mL of 1 M sodium cyanoborohydride solution in THF. The mixture was stirred at rt for 16 h. The reaction was quenched with 5 mL of sat'd $NaHCO_3$ and the resulting mixture was partitioned between 30 mL of ether and 10 mL of water and the layers were separated. The organic layer was dried. The aqueous layer was extracted with 30 mL of ether; the extract was dried and combined with the original organic layer. The combined organic layers were concentrated in vacuo. Flash chromatography on 10 g of silica gel using 100:1 v/v, then 40:1 v/v $CH_2$C12/methanol as the eluant afforded 134 mg (66% from the intermediate aldehyde) of the title compound as a foam.

$^1H$ NMR ($CDCl_3$, 400 MHz, ppm, ranges are given due to amide rotamers and line broadening): δ 1.30–3.90 (15 H), 6.73–6.80 (m, 2 H), 7.05–7.90 (10 H). 2.72 and 3.12 ($—CH_2N(\underline{CH_3})COAr$) Mass Spectrum (FAB): 656 ($^{37}Cl$+$^{35}Cl$ isotope), 654 ($^{35}Cl$+$^{35}Cl$ isotope). Analysis: Calculated for $C_{33}H_{30}Cl_2F_6N_2O$ C, 60.47; H, 4.61; N, 4.27 Found: C, 59.84; H, 4.46; N, 3.97.

EXAMPLE 14

1'-((3S)-(3,4-Dichlorophenyl)-4-(N-methyl)benzamidobutyl)-3,4-dihydro-4-hydroxy-6-methoxy-spiro[2H-1-benzopyran-2,3'-piperidine]

A solution of 51 mg (0.088 mmol) of 1'-((3S)-(3,4-dichlorophenyl)-4-(N-methyl)benzamidobutyl)-3,4-dihydro-4-oxo-6-methoxy-spiro[2H-1-benzopyran-2,3'-piperidine] (EXAMPLE 2) in 1 mL of methanol at 0° C. was treated with 10 mg of sodium borohydride. The resulting mixture was warmed to room temperature and stirred for 30 minutes. The reaction was quenched with 1.0 mL of 2.0 N sodium hydroxide solution and extracted with 3×10 mL of methylene chloride. The organic extracts were combined, dried over sodium sulfate and concentrated to afford 53 mg of the title compound. $^1$H NMR ($CDCl_3$, 400 MHz, ppm, ranges are given due to amide rotamers and line broadening): δ 1.40–5.00 (25 H), 6.70–7.42 (11 H). Mass Spectrum (FAB): 585 ($^{37}$Cl+$^{35}$Cl isotope), 583 ($^{35}$Cl+$^{35}$Cl isotope).

EXAMPLE 15

1'-((3S)-(3,4-Dichlorophenyl)-4-(N-methyl)benzamidobutyl)-3,4-dihydro-4-hydroxy-6-methoxy-spiro[2H-1-benzopyran-2,4'-piperidine]

The title compound was obtained from 1'-((3S)-(3,4-dichlorophenyl)-4-(N-methyl)benzamidobutyl)-3,4-dihydro-4-oxo-6-methoxy-spiro[2H-1-benzopyran-2,4'-piperidine] (EXAMPLE 5) using a procedure analogous to EXAMPLE 14.

$^1$H NMR ($CDCl_3$, 400 MHz, ppm, ranges are given due to amide rotamers and line broadening): δ 1.40–3.58 (20 H), 3.86 (m, 1 H), 4.479 (br s, 1 H), 6.70–7.41 (11 H). 3.75 (3 H, $\underline{CH_3}$O—) Mass Spectrum (FAB): 585 ($^{37}$Cl+$^{35}$Cl isotope), 583 ($^{35}$Cl+$^{35}$Cl isotope).

EXAMPLE 16

1'-((3S)-(3,4-Dichlorophenyl)-4-(N-methyl)benzamidobutyl)spiro-(indane-1,4'-piperidine)

A mixture of 50 mg (0.096 mmol) of 1'-((3S)-(3,4-dichlorophenyl)-4-(N-methyl)benzamidobutyl)spiro(1H-indene-1,4'-piperidine) (EXAMPLE 1) and 7.5 mg 10% palladium on carbon catalyst in 2 mL of absolute ethanol was stirred under an atmosphere of hydrogen for 5 hours. The catalyst was filtered on a pad of Celite, the flask and filtered solids rinsed well with ethanol (20 mL) and the filtrate was concentrated in vacuo. Flash chromatography on 4 g of silica gel afforded 43 mg of the title compound as an oil. $^1$H NMR ($CDCl_3$, 400 MHz, ppm, ranges are given due to amide rotamers and line broadening): δ 1.45–4.05 (22 H), 6.80–7.60 (12 H). Mass Spectrum (FAB): 523 ($^{37}$Cl+$^{35}$Cl isotope), 521 ($^{35}$Cl+$^{35}$Cl isotope).

EXAMPLE 17

1'-(1-Oxo-(3S)-(3,4-dichlorophenyl)-4-(N-methyl)benzamidobutyl)-spiro(1H-indene-1,4'-piperidine)

STEP 1: (3S)-(3,4-Dichlorophenyl)-4-(N-methyl)benzamidobutanoic acid.

A solution of 525 mg (1.5 mmol) of (3S)-(3,4-dichlorophenyl)-4-(N-methyl)benzamidobutanal in 10 mL of 1:1 v/v methanol/1.0 N sodium hydroxide solution was treated with 463 mg (2.0 mmol) of freshly prepared silver oxide and the resulting mixture was stirred at room temperature for 20 hours. The reaction mixture was filtered through a pad of Celite and the flask and filtered solids were washed well with methanol (~25 mL). The filtrate was concentrated to ~10% of the original volume in vacuo and the residue was partitioned between 50 mL of ether and 50 mL of 2.0 N hydrochloric acid solution and the layers were separated. The organic layer was washed with 25 mL of saturated aqueous sodium chloride solution, dried over magnesium sulfate and concentrated in vacuo. Flash chromatography on 30 g of silica gel using 1:1 v/v ethyl acetate/hexanes+1% acetic acid as the eluant afforded 540 mg (98%) of the title compound as a foam. $^1$H NMR ($CDCl_3$, 400 MHz, ppm, ranges are given due to amide rotamers and line broadening): δ 1.20–4.00 (8 H), 6.70–7.45 (8 H). Mass Spectrum (FAB): 368 ($^{37}$Cl+$^{35}$Cl isotope), 366 ($^{35}$Cl+$^{35}$Cl isotope).

STEP 2: 1'-(1-Oxo-(3S)-(3,4-dichlorophenyl)-4-(N-methyl)benzamidobutyl)spiro (1H-indene-1,4'-piperidine).

A solution of 315 mg (0.86 mmol) of (3S)-(3,4-dichlorophenyl)-4-(N-methyl)benzamidobutanoic acid (EXAMPLE 17, STEP 1) in 3 mL of methylene chloride was treated with 0.5 mL of oxalyl chloride and 1 drop of N,N-dimethylformamide. The resulting solution was stirred at room temperature for 20 minutes, then concentrated in vacuo. The residue was twice redissolved in 10 mL of ether and concentrated in vacuo. A solution of the crude acid chloride in 5 mL of methylene chloride was slowly added to a solution of 300 mg (1.62 mmol) of spiro(1H-indene-1,4'-piperidine) and 0.52 mL (3.0 mmol) of N,N-diisopropylethyl amine in 5 mL of methylene chloride at 0° C. and the resulting solution was stirred cold for 1 hour. The reaction mixture was diluted with 40 mL of ethyl acetate and washed with 20 mL of 2.0 N hydrochloric acid solution, 20 mL of saturated aqueous sodium bicarbonate solution, 20 mL of saturated sodium chloride solution, dried over magnesium sulfate and concentrated in vacuo. Flash chromatography on 25 g of silica gel using 7:3 v/v, then 1:1 v/v methylene chloride/ethyl acetate as the eluant afforded 302 mg (66%) of the title compound as a foam. $^1$H NMR ($CDCl_3$, 400 MHz, ppm, ranges are given due to amide rotamers and line broadening): d 1.20–2.00 (5 H), 2.40–4.70 (11 H), 6.79 (app s, 2 H), 6.85–7.55 (12 H). Mass Spectrum (FAB): 535 ($^{37}$Cl+$^{35}$Cl isotope), 533 ($^{35}$Cl+$^{35}$Cl isotope).

EXAMPLE 18

1'-((3S)-(3,4-Dichlorophenyl)-(4)-((N-methyl)benzamido)pentyl)spiro-(1H-indene-1,4'-piperidine)

STEP 1: N-Methoxy-N-methyl-(2S)-(3,4-dichlorophenyl)-4-pentenamide.

A mixture of 306 mg (1.25 mmol) of (2S)-(3,4-dichlorophenyl)-4-pentenoic acid and 202 mg (1.50 mmol) of 1-hydroxybenzotriazole hydrate in 10 mL of methylene chloride was cooled to 0° C. and treated with 287 mg (1.50 mmol) of 1-(3-dimethylaminopropyl)-3-ethylcarbodiimide. The cooling bath was removed and after 45 min. a solution of 365 mg (3.75 mmol) of N,O-dimethylhydroxylamine hydrochloride and 522 μl (3.75 mmol) of triethylamine in 10 mL of methylene chloride was added via cannula. The mixture was then stirred at 22° C. for 4 hours and then quenched with 10 mL of water and diluted with 8 mL of methylene chloride. The layers were separated and the aqueous layer was extracted with methylene chloride (2×10 mL). The combined organic layers were washed with 10 mL of brine, dried over anhydrous sodium sulfate, filtered, and concentrated in vacuo. Flash chromatography on 75 g of silica gel using 1:9 v/v ethyl acetate/hexane as the eluant afforded 319 mg (89%) of the title compound as a clear oil.

$^1$H-NMR (400 MHz, $CDCl_3$) δ 2.40 (pentet, 1H), 2.75 (pentet, 1H), 3.13 (s, 3H), 3.52 (s, 3H), 3.99–4.01 (m, 1H), 4.96–5.05 (m, 2H), 5.63–5.70 (m, 1H), 7.15 (dd, 1H), 7.35 (d, 1H), 7.41 (d, 1H). Mass Spectrum (FAB): m/z 290 (M+H, $^{37}$Cl+$^{35}$Cl isotope, 50%), 288 (M+H, $^{37}$Cl+$^{37}$Cl isotope, 100%).

STEP 2: (3S)-(3,4-dichlorophenyl)-5-hexen-2-one.

A solution of 319 mg (1.11 mmoL) of N-methoxy-N-methyl-(2S)-(3,4-dichlorophenyl)-4-pentenamide (EXAMPLE 18, STEP 1) in 10 mL of dry tetrahydrofuran was cooled to −70° C. and treated with 1.0 mL (1.40 mmol) of methyllithium and stirred between −70° C. to −40° C. After 3 hours, the reaction was quenched with 5 mL of water, and diluted with 10 mL of ethyl acetate. The layers were separated and the organic layer was washed with water (3×10 mL). The aqueous layers were extracted with 10 mL of ethyl acetate. The combined organic layers were washed with 10 mL of saturated aqueous sodium chloride solution, dried over anhydrous sodium sulfate, filtered, and concentrated in vacuo. Flash chromatography on 44 g of silica gel using 1:3 v/v ethyl acetate/hexane as the eluant afforded 250 mg (93%) of the title compound as a clear oil. $^1$H-NMR (400 MHz, $CDCl_3$) δ 2.07 (s, 3 H), 2.36 (pentet, 1 H), 2.72 (pentet, 1 H), 3.64 (t, 1 H), 4.95–5.01 (m, 2 H), 5.55–5.65 (m, 1 H), 7.03 (dd, 1 H), 7.30(d, 1 H), 7.39 (d, 1 H). Mass Spectrum (FAB): m/z 245 (M+H, $^{37}$Cl+$^{35}$Cl isotope, 30%), 243 (M+H, $^{37}$Cl+$^{37}$Cl isotope, 50%), 155 (60%), 119 (100%).

STEP 3: N-Methyl-(3S)-(3,4-dichlorophenyl)-5-hexen-2-amine.

A mixture of 102 mg (0.42 mmoL) of (3S)-(3,4-dichlorophenyl)-5-hexen-2-one (EXAMPLE 18, STEP 2), 170 mg (2.52 mmol) of methylamine hydrochloride, and 234 μl (1.68 mmol) of triethylamine in 4.0 mL of methanol was treated with 16 mg (0.25 mmol) of sodium cyanoborohydride and stirred at 22° C. for 20 hours. Saturated aqueous sodium bicarbonate solution (1.0 mL) was added and the resulting milky mixture was diluted with 5.0 mL of ethyl acetate and 5.0 mL of water. The layers were separated and the organic layer was washed with water (3×5 mL). The aqueous layers were extracted with 10 mL of ethyl acetate. The combined organic layers were washed with 10 mL of saturated aqueous sodium chloride solution, dried over anhydrous sodium sulfate, filtered, and concentrated in vacuo. Flash chromatography on 42 g of silica gel using 10:1 v/v ether/hexane as the eluant afforded 64 mg of the higher $R_f$ isomer (Isomer A) and 22 mg of a lower $R_f$ isomer (Isomer B) both as yellow oils. $^1$H-NMR (400 MHz, $CDCl_3$); Isomer A: δ 1.04 (d, 3 H), 2.29–2.35 (m, 4 H), 2.50–2.68 (m, 3 H), 4.86–4.95 (m, 2 H), 5.48–5.56 (m, 1 H), 7.01 (dd, 1 H), 7.26 (d, 1 H), 7.34 (d, 1 H); Isomer B: d 0.86 (d, 3 H), 2.32–2.50 (m, 4 H), 2.51–2.53 (m, 1 H), 2.68–2.73 (m, 2 H), 4.88–4.98 (m, 2 H), 5.54–5.61 (m, 1 H), 6.97 (dd, 1 H), 7.22 (d, 1 H), 7.33 (d, 1 H). Mass Spectrum (Isomer A) (FAB): m/z 260 (M+H, $^{37}$Cl+$^{35}$Cl isotope, 70%), 258 (M+H, $^{35}$Cl+$^{35}$Cl isotope, 100%).

STEP 4: N-Methyl-N-((2)-((3S)-(3,4-dichlorophenyl))-5-hexenyl)benzamide.

A solution of 197 mg (0.76 mmol) of N-methyl (3S)-(3,4-dichlorophenyl)-5-hexen-2-amine (Isomer A) (EXAMPLE 18, STEP 3) in 7.0 mL of dry methylene chloride was cooled to −70° C. and treated with 160 μl (1.14 mmol ) of triethylamine and 177 μl (1.53 mmol) of benzoyl chloride. The cooling bath was removed and the reaction was stirred at 22° C. for 20 hours. The reaction was quenched with 3.0 mL of water and diluted with 8.0 mL of methylene chloride. The layers were separated and the aqueous layer was extracted with methylene chloride (2×5 mL). The combined organic layers were washed with 10 mL of brine, dried over anhydrous sodium sulfate, filtered, and concentrated in vacuo. Flash chromatography on 43 g of silica gel using 1:3 v/v ethyl acetate/hexane as the eluant afforded 261 mg (95%) of the title compound as a clear oil.

$^1$H-NMR (400 MHz, $CDCl_3$, ranges are given due to amide rotamers and line broadening) δ 1.38–5.55 (13H), 6.70–7.38 (9H). Mass Spectrum (FAB): m/z 364 (M+H, $^{37}$Cl+$^{35}$Cl isotope, 100%), 362 (M+H, $^{35}$Cl+$^{35}$Cl isotope, 70%).

STEP 5: (3S)-(3,4-Dichlorophenyl)-(4)-(N-methyl) benzamidopentanal.

A solution of 261 mg (0.72 mmol) of N-methyl-N-((2?)-((3S)-(3,4-dichlorophenyl))-5-hexenyl)benzamide (EXAMPLE 18, STEP 4) in 4.0 mL of 2:1:1 v/v/v acetone/t-butanol/water was treated with 1.8 mg (0.01 mmol) of osmium tetroxide. After 5 min., 128 mg (1.08 mmol) of N-methylmorpholine N-oxide was added and the resulting mixture was stirred at 22° C. for 2 hours. The reaction was quenched with 84 mg of sodium bisulfite and concentrated in vacuo to 25% of the original volume. The residue was partitioned between 10 mL of methylene chloride and 15 mL of water and the layers were separated. The aqueous layer was extracted with methylene chloride (2×5 mL). The combined organic layers were dried over anhydrous sodium sulfate, filtered, and concentrated in vacuo.

A solution of the crude diol in 6.0 mL of 3:1 v/v THF/water was treated with 194 mg (0.90 mmol) of sodium periodate. After 30 min., the reaction mixture was partitioned between 10 mL of ethyl ether and 10 mL of water and the layers were separated. The organic layer was washed with water (2×10 mL), dried over anhydrous sodium sulfate, filtered, and concentrated in vacuo. The residue was filtered through a pad of 76 g of silica gel using ethyl ether as the eluant to afford 183 mg (70%) of the title compound as an oil.

$^1$H-NMR (400 MHz, $CDCl_3$, ranges are given due to amide rotamers and line broadening) δ 1.33 (d, 3 H), 2.55 (s, 3 H), 2.81–2.89 (m, 3 H), 3.30–3.50 (m, 2 H), 4.90–5.10 (m, 1 H), 6.79–7.41 (m, 9 H), 9.50 (s, 1 H), 9.65 (s, 1 H). Mass Spectrum (FAB): m/z 366 (M+H, $^{37}$Cl+$^{35}$Cl isotope, 45%), 364 (M+H, $^{37}$Cl+$^{37}$Cl isotope, 65%), 242 (58%), 162 (100%), 136 (52%), 105 (53%).

STEP 6: 1'-((2)-((3S)-(3,4-Dichlorophenyl)-5-(N-methyl) benzamido)-pentyl) spiro(1H-indene-1,4'-piperidine).

A mixture of 70 mg (0.19 mmol) of (3S)-(3,4-dichlorophenyl)-(4)-(N-methyl)benzamidopentanal (EXAMPLE 18, STEP 5), 62 mg (0.28 mmol) of spiro(1H-indene-1-4'-piperidine) hydrochloride in 3.0 mL of methanol was treated with 36 mg (0.58 mmol) of sodium cyanoborohydride and stirred at 22° C. for 20 hours. Saturated sodium bicarbonate solution (1.0 mL) was added and the resulting milky mixture was concentrated to 50% of its original volume. The residue was partitioned between 20 mL of ethyl acetate and 10 mL of water and the layers were separated. The organic layer was washed with water (3×10 mL). The aqueous layers were extracted with 10 mL of ethyl acetate. The combined organic layers were washed with 10 mL of saturated aqueous sodium chloride solution, dried over anhydrous sodium sulfate, filtered, and concentrated in vacuo. Flash chromatography on 43 g of silica gel using 5:95 v/v methanol/methylene chloride as the eluant afforded 83 mg (81%) of the title compound as a white foam. $^1$H-NMR (400 MHz, $CDCl_3$, ranges are given due to amide rotamers and line broadening) δ 1.22–5.11 (20 H), 6.68–7.42 (m, 15 H). Mass Spectrum (FAB): m/z 569 (M+H, $^{37}$Cl+$^{35}$Cl isotope, 70%), 567 (M+H, $^{35}$Cl+$^{35}$Cl isotope, 100%).

EXAMPLE 19

1'-((2)-((3S)-(3,4-Dichlorophenyl)-5-(N-methyl) benzamido)pentyl) spiro(1-indane-1,4'-piperidine)

The title compound was prepared from 1'-((2)-((3S)-(3,4-dichlorophenyl)-5-(N-methyl)benzamido)pentyl) spiro (1H-indene-1,4'-piperidine) (EXAMPLE 18) using a procedure identical to EXAMPLE 16. $^{1}$H-NMR (400 MHz, $CDCl_3$, ranges are given due to amide rotamers and line broadening) δ 1.36–5.28 (24 H), 6.77 (d, 2 H), 7.04–7.40 (m, 13 H).Mass Spectrum (FAB): m/z 538 (M+H, $^{37}$Cl+$^{35}$Cl isotope, 70%), 536 (M+H, $^{35}$Cl+$^{35}$Cl isotope, 100%).

EXAMPLE 20

1'-((3S)-(3,4-Dichlorophenyl)-(4)-((N-methyl)benzamido) octyl)spiro-(1H-indene-1,4'-piperidine)

The title compound was prepared in 6 steps from (2S)-(3,4-dichlorophenyl)-4-pentenoic acid using procedures identical to those in EXAMPLE 18, substituting butyllithium for methyllithium in EXAMPLE 18, STEP 2. $^{1}$H-NMR (400 MHz, $CDCl_3$, ranges are given due to amide rotamers and line broadening) δ 0.92 (t, 3 H), 1.20–3.00 (24 H), 6.69–6.90 (m, 4 H), 7.15–7.41 (m, 10 H). Mass Spectrum (FAB): m/z 578 (M+H, $^{37}$Cl+$^{35}$Cl isotope, 70%), 576 (M+H, $^{35}$Cl+$^{35}$Cl isotope, 100%).

EXAMPLE 21

1'-((4)-((3S)-(3,4-Dichlorophenyl)-1-(N-methyl) benzamido)octyl)spiro(1H-indene-1,4'-piperidine)

The title compound was prepared from 1'-((4)-((3S)-(3,4-dichlorophenyl)-1-(N-methyl)benzamido)octyl)spiro(1H-indene-1,4'-piperidine) (EXAMPLE 20) using a procedure identical to EXAMPLE 16.

$^{1}$H-NMR (400 MHz, $CDCl_3$, ranges are given due to amide rotamers and line broadening) δ 0.92 (t, 3 H), 1.35–2.87 (27 H), 6.75 (d, 2 H), 7.12–7.40 (m, 10 H).Mass Spectrum (FAB): m/z 580 (M+H, $^{37}$Cl+$^{35}$Cl isotope, 70%), 578 (M+H, $^{35}$Cl+$^{35}$Cl isotope, 100%).

Employing standard acylation procedures on 1'-[3-((S)-(3,4-dichlorophenyl))-4-(methylamino)butyl]-spiro[1H-indene-1,4'-piperidine (for example, as in Example 13, Step 1, or Example 18, Step 1), the following compounds were prepared:

EXAMPLE 22

1'-((3S)-(3,4-Dichlorophenyl)-4-((N-methyl)thiophene-2-carboxamido-butyl)spiro[1H-indene-1,4'-piperidine]

Mass Spectrum (FAB): m/Z 140,197,227,229,383,525

EXAMPLE 23

1'-((3S)-(3,4-Dichlorophenyl)-4-((N-methyl) benzenesulfonamidobutyl) spiro[1H-indene-1,4'-piperidine]

Mass Spectrum (FAB): m/Z 140,197,227,229,383,555, 557

EXAMPLE 24

1'-((3S)-(3,4-Dichlorophenyl)-4-((N-methyl)furan-2-carboxamidobutyl) spiro[1H-indene-1,4'-piperidine]

Mass Spectrum (FAB): m/Z 140,197,227,229,383,509, 511

EXAMPLE 25

1'-((3S)-(3,4-Dichlorophenyl)-4-((N-methyl) phenoxycarboxamidobutyl) spiro[1H-indene-1,4'-piperidine]

Mass spectrum (FAB): mn/Z 140,197,227,229,383,535, 538

EXAMPLE 26

1'-((3S)-(3,4-Dichlorophenyl)-4-((N-methyl) phenylaminocarboxamido butyl)spiro[1H-indene-1,4'-piperidine]

Mass Spectrum (FAB): m/Z 140,197,227,229,383,534, 536

EXAMPLE 27

1'-((3S)-(3,4-Dichlorophenyl)-4-((N-methyl)pyridine-2-carboxamidobutyl)spiro[1H-indene-1,4'-piperidine]

Mass Spectrum (FAB): m/Z 140,197,227,229,383,520, 522

EXAMPLE 28

1'-((3S)-(3,4-Dichlorophenyl)-4-((N-methyl)pyridine-3-carboxamidobutyl)spiro[1H-indene-1,4'-piperidine]

Mass Spectrum (FAB): m/Z 140,197,227,229,383,520, 522

EXAMPLE 29

1'-((3S)-(3,4-Dichlorophenyl)-4-((N-methyl)pyridine-4-carboxamidobutyl)spiro[1H-indene-1,4'-piperidine]

Mass Spectrum (FAB): m/Z 140,197,227,229,383,520, 522

EXAMPLE 30

1'-((3S)-(3,4-Dichlorophenyl)-4-((N-methyl) benzothiophene-2-carboxamidobutyl)spiro[1H-indene-1,4'-piperidine]

Mass Spectrum (FAB): m/Z 197,227,229,383,575,577

EXAMPLE 31

1'-((3S)-(3,4-Dichlorophenyl)-4-((N-methyl)thiophene-2-acetamidobutyl)spiro[1H-indene-1,4'-piperidine]

Mass Spectrum (FAB): m/Z 141,197,227,229,383,539, 541

EXAMPLE 32

1'-((3S)-(3,4-Dichlorophenyl)-4-((N-methyl)thiophene-3-carboxamidobutyl)spiro[1H-indene-1,4'-piperidine]

Mass Spectrum (FAB): m/Z 141,197,227,229,383,525, 526

EXAMPLE 33

1'-((3S)-(3,4-Dichlorophenyl)-4-((N-methyl)-(3-methylthiophene-2-carboxamido)butyl)spiro[1H-indene-1, 4'-piperidine]

Mass Spectrum (FAB): m/Z 197,227,229,383,539,541

EXAMPLE 34

1'-((3S)-(3,4-Dichlorophenyl)-4-((N-methyl)-(5-methylthiophene-2-carboxamido)butyl)spiro[1H-indene-1, 4'-piperidine]

Mass Spectrum (FAB): m/Z 141,197,227,229,383,539, 541

EXAMPLE 35

1'-((3S)-(3,4-Dichlorophenyl)-4-((N-methyl)-(5-chlorothiophene-2-carboxamido)butyl)spiro[1H-indene-1, 4'-piperidine]

Mass Spectrum (FAB): m/Z 197,227,229,383,559,561 (cluster)

EXAMPLE 36

1'-((3S)-(3,4-Dichlorophenyl)-4-((N-methyl)-(2,3-dibromothiophene-5-carboxamido)butyl)spiro[1H-indene-1,4'-piperidine]

Mass Spectrum (FAB): m/Z 140,197,227,229,383,682 (cluster)

EXAMPLE 37

3-(S)-(3,4-Dichlorophenyl)-4-((t-butoxycarbonyl) methylamino)butanal.

A solution of 10 g (41 mmol) of 3-(S)-(3,4-dichlorophenyl)-4-methylamino-1-pentene in 100 mL of CH2Cl2 was cooled in ice bath and treated with 5.8 mL (41 mmol) of triethylamine (Et3N) and 9 g (41 mmol) of di-t-butyl dicarbonate. The cold bath was removed after 5 min and the stirring was continued for 1 h. The reaction mixture was diluted with CH2Cl2 and washed with water, 1.2 N HCl, saturated NaHCO3 and brine. The solution was dried over Na2SO4 and concentrated to give 14.58 g of resiual oil. $^1$H NMR (CDCl3, ppm ranges are given because of amide rotomers and line broadening) δ 1.36 (s, 9 H), 2.33 (m, 2 H), 2.60& 2.70 (2s, 3 H), 2.8–3.6 (m, 3 H), 4.94 (m, 2 H), 5.59 (m, 1 H), 6.9–7.4 (m, 3 H). The residue was dissolved in 80 mL of acetone, 40 mL of t-butanol and 40 mL of water. To this solution 1 mL of Osmium tetroxide (4% solution in water) and 5.15 g (44 mmol) of 4-methylmorpholine N-oxide were added. After stirring for 26 h, the reaction was quenched with approximately 5 g of Na2SO3 and concentrated to 25% of the original volume. The residue was partitioned between water and 1:1 ether (Et2O), ethyl acetate (EtOAc), the layers were separated and the aqueous layer was extracted with Et2O:EtOAc. Each organic layer was washed with water, brine and dried by filtering through Na2SO4. The filtrate was concentrated to afford the crude diol. A solution of the diol in 120 mL of tetrahydrofuran (THF) and 40 mL of water was treated with 9.42 g (44 mmol) of sodium periodate. After stirring for 2 h, the reaction was diluted with Et2O:EtOAC and washed with water and brine. The organic layer was dried (Na2SO4) and the filtrate was concentrated. The residue was purified by prep LC using 30% EtOAC/hexane to furnish 11.74 g (83% yield for three steps) of the title compound as a thick oil. $^1$H NMR (CDCl3, ppm ranges are given because of amide rotomers and line broadening) δ 1.38 (s, 9 H), 2.69 & 2.75 (2s, 3 H), 2.6–3.65 (m, 5 H), 6.95–7.4 (m, 3 H), 9.67 (s, 1 H).

EXAMPLE 38

1'-[3-(S)-(3,4-dichlorophenyl)-4-(t-butoxycarbonyl (methylamino))-butyl]-spiro(1H-indene-1,4'-piperidine).

To a solution of 3.46 g (10 mmol) of 3-(S)-(3,4-dichlorophenyl)-4-(t-butoxycarbonyl-methylamino)butanal (Example 1) in 20 mL of methanol were added 3.11 g (14 mmol) of spiro(1H-indene-1,4'-piperidine) hydrochloride and 3 g of powdered 4 Å molecular sieves. After 15 min a solution of 2.52 g (40 mmol) of NaCNBH3 in 30 mL of THF was dropwise added. Some gas evolution was observed. After stirring the reaction overnight, the mixture was filtered through a pad of celite, the reaction flask and the pad were rinsed with methanol. The filtrate was concentrated to approximately 10 ml and the residue was partitioned between saturated NaHCO3 and Et2O:EtOAC. The organic layer was washed with water, brine and dried over NA2SO4. The filtrate was concentrated and the residue was chromatographed on a flash column using a gradient of 49:49:2 to 98:0:2 EtOAc: Hexane: triethylamine to furnish 4.05 g (79%) of the title compound as a foam.

$^1$H NMR (CDCl3, ppm ranges are given because of amide rotomers and line broadening) δ 1.37 (s, 9 H), 1.5–3.6 (m, 15 H), 2.63 & 2.73 (2 s, 3 H), 6.70 (d, 1 H, J=6 Hz), 6.77 (d, 1 H, J=6 Hz), 6.95–7.4 (m, 7 H).

EXAMPLE 39

1'-[3-(S)-(3,4-dichlorophenyl)-4-(N-(3,5-dichloro)benzoyl-(methylamino))butyl]-spiro(1H-indene-1,4'-piperidine].

Step A: 1'[3-((S)-(3,4-dichlorophenyl))-4-(methylamino) butyl]-spir[1-H-indene-1,4'-piperidine].

Cold trifluoroacetic acid (TFA, 5 mL) and 0.2 mL of anisole were added to 0.565 g (1.1 mmol) of 1'[3-(S)-(3,4-dichlorophenyl)-4-(t-butoxycarbonyl(methylamino))butyl]-spiro(1H-indene-1,4'-piperidine) and the mixture was stirred in ice bath until all the foam dissolved. After stirring the resulting solution at room temperature for 30 min, it was concentrated in vacuo. The residue was partitioned between dilute NaOH (ca. 0.5 N) and CH2Cl2 and the layers were separated. The organic layer was washed with brine, dried over Na2SO4 and concentrated to give 0.523 g of foam which was used in the next step without purification. $^1$H NMR (CDCl3, ppm ranges are given because of amide rotomers and line broadening) δ 1.7–2.7 (m, 10 H), 2.64 (s, 3 H), 2.88 (s, 3 H), 2.9–3.4 (m, 5 H), 3.70 (s, 2H), 6.8–7.4 (m, 7 H).

Step B: 1'[3-(S)-(3,4-dichlorophenyl)-4-(N-(3,5-dichloro) benzoyl-(methylamino))butyl]-spiro(1H-indene-1,4'-piperidine)

A solution of 0.105 g (0.55 mmol) of 3,5-dichlorobenzoic acid in 1 mL of CH2Cl2 and 2 drops of DMF was treated with 54 μL of oxalyl chloride. (Gas evolution!) After 20 min the solution was concentrated in vacuo and the residue was mixed with 0.152 g (0.36 mmol) of 1'[3-((S)-(3,4-dichlorophenyl))-4-(methylamino)butyl]-spiro[1H-indene-1,4'-piperidine obtained from step A, and 0.1 mL (0.71 mmol) of Et3N in 2 mL of CH2Cl2. After 1 h the reaction mixture was diluted with CH2Cl2 and washed with saturated NaHCO3, water, and brine. The CH2Cl2 solution was dried over Na2SO4, filtered and concentrated. Purification of the residue by prep TLC using 10% methanol-EtOAc afforded 0.18 g (84% yield) of the title compound as a foam. $^1$H NMR (CDCl3, ppm ranges are given because of amide rotomers and line broadening) δ 1.6–2.4 (m, 10 H), 2.27 (s, 6 H), 2.6–3.9 (m, 10 H), 2.86 (s, 3 H), 6.6–7.5 (m, 10 H). Mass Spectrum (FAB) 589($^{37}$Cl+$^{35}$Cl isotope), 587($^{35}$Cl+$^{35}$Cl isotope).

The following compounds were prepared by substituting the required acid chloride for 3,5-dichlorobenzoyl chloride in step B.

EXAMPLE 40

1'-[3-(S)-(3,4-dichlorophenyl)-4-(N-(3-chloro)benzoyl-(methylamino))butyl]-spiro(1H-indene-1,4'-piperidine)

Mass Spectrum (FAB) 555($^{37}$Cl+$^{35}$Cl isotope), 553($^{35}$Cl+$^{35}$Cl isotope).

EXAMPLE 41

1'-[3-(S)-(3,4-dichlorophenyl)-4-(N-(3-trifluoromethyl) benzoyl-(methylamino))butyl]-spiro(1H-indene-1,4'-piperidine)

Mass Spectrum (FAB) 589($^{37}$Cl+$^{35}$Cl isotope), 587($^{35}$Cl+$^{35}$Cl isotope).

EXAMPLE 42

1'-[3-(S)-(3,4-dichlorophenyl)-4-(N-(3-isopropyloxy) benzoyl-(methylamino))butyl]-spiro(1H-indene-1,4'-piperidine)

Mass Spectrum (FAB) 579($^{37}$Cl+$^{35}$Cl isotope), 577($^{35}$Cl+$^{35}$Cl isotope).

EXAMPLE 43

1'-[3-(S)-(3,4-dichlorophenyl)-4-(N-(3-isopropyloxy) phenylacetyl-(methylamino))butyl]-spiro(1H-indene-1,4'-piperidine)

Mass Spectrum (FAB) 593($^{37}$Cl+$^{35}$Cl isotope), 591($^{35}$Cl+$^{35}$Cl isotope).

EXAMPLE 44

1'-[3-(S)-(3,4-dichlorophenyl)-4-(N-(4-t-butyl)benzoyl-(methylamino))butyl]-spiro(1H-indene-1,4'-piperidine)

Mass Spectrum (FAB) 577($^{37}$Cl+$^{35}$Cl isotope), 575($^{35}$Cl+$^{35}$Cl isotope).

EXAMPLE 45

1'-[3-(S)-(3,4-dichlorophenyl)-4-(N-(2-phenyl)benzoyl-(methylamino))butyl]-spiro(1H-indene-1,4'-piperidine)

Mass Spectrum (FAB) 597($^{37}$Cl+$^{35}$Cl isotope), 595($^{35}$Cl+$^{35}$Cl isotope).

EXAMPLE 46

1'-[3-(S)-(3,4-dichlorophenyl)-4-(N-(1-naphthoyl)-(methylamino))butyl]-spiro(1H-indene-1,4'-piperidine)

Mass Spectrum (FAB) 571($^{37}$Cl+$^{35}$Cl isotope), 569($^{35}$Cl+$^{35}$Cl isotope).

EXAMPLE 47

1'-[3-(S)-(3,4-dichlorophenyl)-4-(N-(2-naphthoyl (methylamino))butyl]-spiro(1H-indene-1,4'-piperidine)

Mass Spectrum (FAB) 571($^{37}$Cl+$^{35}$Cl isotope), 569($^{35}$Cl+$^{35}$Cl isotope).

EXAMPLE 48

1'-[3-(S)-(3,4-dichlorophenyl)-4-(N-(2-methyl)benzoyl-(methylamino))butyl]-spiro(1H-indene-1,4'-piperidine)

Mass Spectrum (FAB) 535 ($^{37}$Cl+$^{35}$Cl isotope, M+1), 533 ($^{35}$Cl+$^{35}$Cl isotope, M+1).

EXAMPLE 49

1'-[3-(S)-(3,4-dichlorophenyl)-4-(N-(4-methyl)benzoyl-(methylamino))butyl]-spiro(1H-indene-1,4'-piperidine)

Mass Spectrum (FAB) 535 ($^{37}$Cl+$^{35}$Cl isotope, M+1), 533($^{35}$Cl+$^{35}$Cl isotope, M+1).

EXAMPLE 50

1'-[3-(S)-(3,4-dichlorophenyl)-4-(N-(3-methyl)benzoyl-(methylamino))butyl]-spiro(1H-indene-1,4'-piperidine).

Mass Spectrum (FAB) 535 ($^{37}$Cl+$^{35}$Cl isotope), 533 ($^{35}$Cl+$^{35}$Cl isotope, M+1).

EXAMPLE 51

1'-[3-(S)-(3,4-dichlorophenyl)-4-(N-(3,5-dimethyl)benzoyl-(methylamino))butyl]-spiro(1H-indene-1,4'-piperidine)

Mass Spectrum (FAB) 549 ($^{37}$Cl+$^{35}$Cl isotope), 547 ($^{35}$Cl+$^{35}$Cl isotope).

EXAMPLE 52

1'-[3-(S)-(3,4-dichlorophenyl)-4-(N-(2,3-dimethyl)benzoyl-(methylamino))butyl]-spiro(1H-indene-1,4'-piperidine)

Mass Spectrum (FAB) 549 ($^{37}$Cl+$^{35}$Cl isotope), 547 ($^{35}$Cl+$^{35}$Cl isotope).

EXAMPLE 53

1'-[3-(S)-(3,4-dichlorophenyl)-4-(N-(3,4-dimethyl)benzoyl-(methylamino))butyl]-spiro(1H-indene-1,4'-piperidine)

Mass Spectrum (FAB) 549 ($^{37}$Cl+$^{35}$Cl isotope), 547 ($^{35}$Cl+$^{35}$Cl isotope).

EXAMPLE 54

1'-[3-(S)-(3,4-dichlorophenyl)-4-(N-(2,5-dimethyl)benzoyl-(methylamino))butyl]-spiro(1H-indene-1,4'-piperidine)

Mass Spectrum (FAB) 549 ($^{37}$Cl+$^{35}$Cl isotope), 547 ($^{35}$Cl+$^{35}$Cl isotope).

EXAMPLE 55

1'-[3-(S)-(3,4-dichlorophenyl)-4-(N-(2,4-dimethyl)benzoyl-(methylamino))butyl]-spiro(1H-indene-1,4'-piperidine)

Mass Spectrum (FAB) 549 ($^{37}$Cl+$^{35}$Cl isotope), 547 ($^{35}$Cl+$^{35}$Cl isotope).

EXAMPLE 56

1'-[3-(S)-(3,4-dichlorophenyl)-4-(trifluoroacetyl (methylamino))butyl]-spiro(1H-indene-1,4'-piperidine)

Mass Spectrum (FAB) 512($^{37}$Cl+$^{35}$Cl isotope), 510($^{35}$Cl+$^{35}$Cl isotope).

EXAMPLE 57

1'-[3-(S)-(3,4-dichlorophenyl)-4-(t-butylcarbonyl (methylamino))butyl]-spiro(1H-indene-1,4'-piperidine)

Mass Spectrum (FAB) 501 ($^{37}$Cl+$^{35}$Cl isotope), 499 ($^{35}$Cl+$^{35}$Cl isotope).

EXAMPLE 58

1'-[3-(S)-(3,4-dichlorophenyl)-4-(1-adamentanecarbonyl (methyl-amino))butyl]-spiro(1H-indene-1,4'-piperidine)

Mass Spectrum (FAB) 579 ($^{37}$Cl+$^{35}$Cl isotope), 577 ($^{35}$Cl+$^{35}$Cl isotope).

EXAMPLE 59

1'-[3-(S)-(3,4-dichlorophenyl)-4-(cyclohexanecarbonyl (methyl-amino))butyl]-spiro(1H-indene-1,4'-piperidine)

Mass Spectrum (FAB) 527 ($^{37}$Cl+$^{35}$Cl isotope), 525 ($^{35}$Cl+$^{35}$Cl isotope).

EXAMPLE 60

1'-[3-(S)-(3,4-dichlorophenyl)-4-(N-(3-methyl)benzoyl-(methylamino))butyl]-spiro[indane-1,4'-piperidine]

A mixture of 50 mg (0.093 mmol) of 1'[3-(S)-(3,4-dichlorophenyl)-4-(N-(3-methyl)benzoyl-(methylamino)) butyl]-spiro(1H-indene-1,4'-piperidine).(Example 50) and 10 mg of 10% palladium on carbon catalyst in 1 mL of ethanol was hydrogenated on a Parr apparatus. After 30 min the catalyst was filtered on a pad of celite and the filtered solids were washed with EtOAc. The filtrate was concentrated in vacuo and the residue was purified by prep TLC using 2% Et3N/EtOAc to isolate 35 mg of the title compound as a foam. (Mass Spectrum (FAB) 537 ($^{37}$Cl+$^{35}$Cl isotope), 535 ($^{35}$Cl+$^{35}$Cl isotope).

EXAMPLE 61

1'-[3-(S)-(3,4-dichlorophenyl)-4-(N-(3,5-dimethyl)benzoyl-(methylamino))butyl]-spiro[indane-1,4'-piperidine]

The title compound was prepared from 1'[3-(S)-(3,4-dichlorophenyl)-4-(N-(3,5-dimethyl)benzoyl-(methylamino))butyl]-spiro(1H-indene-1,4'-piperidine). (Example 51) by following the procedure of example 24. Mass Spectrum (FAB) 551 ($^{37}$Cl+$^{35}$Cl isotope), 549 ($^{35}$Cl+$^{35}$Cl isotope).

EXAMPLE 62

1'-[3-(S)-(3,4-dichlorophenyl)-4-(N-(3,5-bistrifluoromethyl)benzoyl-(methylamino))butyl]-spiro[(3-indanone)-1,4'-piperidine]

A solution of 98 mg (0.2 mmol) of 3-(S)-(3,4-dichlorophenyl)-4-((3,5-bistrifluoromethyl)benzoyl (methylamino))butanal and 44 mg (0.22 mmol) of spiro[(3-indanone)1,4'-piperidine in 2 mL of methanol was treated with 4 $\mu$L of HOAC and 0.2 g of powdered molecular sieves. After stirring for 1 h, 0.6 mL of 1 M NaCNBH3 in THF was dropwise added and the resulting mixture was stirred for 30 min. The reaction was filtered through a pad of celite, the flask and the filtered solids were rinsed with EtOAc. The filtrate was diluted with EtOAc, washed with saturated NaHCO3, water, brine and dried over Na2SO4. The filtrate was concentrated and the residue was chromatographed on a prep TLC plate using 2% Et3N/EtOAc to furnish 51 mg (38% yield) of the title compound. Mass Spectrum (FAB) ($^{37}$Cl+$^{35}$Cl isotope), ($^{35}$Cl+$^{35}$Cl isotope).

The following compounds were synthesized by an analogous procedure using the required aldehyde for the 3-(S)-(3,4-dichlorophenyl)-4-((3,5-bistrifluoromethyl)benzoyl (methylamino))-butanal.

EXAMPLE 63

1'-[3-(S)-(3,4-dichlorophenyl)-4-(N-benzoyl-(methylamino))butyl]-spiro[(3-indanone)-1,4'-piperidine]

Mass Spectrum (FAB) 537 ($^{37}$Cl+$^{35}$Cl isotope), 535 ($^{35}$Cl+$^{35}$Cl isotope).

EXAMPLE 64

1'-[3-(S)-(3,4-dichlorophenyl)-4-(N-(3,5-dimethyl)benzoyl-(methylamino))butyl]-spiro[(3-indanone)-1,4'-piperidine]

Mass Spectrum (FAB) 565 ($^{37}Cl+^{35}Cl$ isotope), 563 ($^{35}Cl+^{35}Cl$ isotope).

EXAMPLE 65

1'-[3-(S)-(3,4-dichlorophenyl)-4-(t-butoxycarbonyl (methylamino))-butyl]-spiro[(3-indanone)-1,4'-piperidine].

Mass Spectrum (FAB) 533 ($^{37}Cl+^{35}Cl$ isotope), 531 ($^{35}Cl+^{35}Cl$ isotope).

EXAMPLE 66

1'-[3-(S)-(3,4-dichlorophenyl)-4-(N-(3,5-dichloro)benzoyl-(methylamino))butyl]-spiro[(3-indanone)-1,4'-piperidine]

Step A: 1'[3-(S)-(3,4-dichlorophenyl)-4-(methylamino) butyl]-spiro[(3-indanone)-1,4'-piperidine].

Treatment of 0.58 g (1.09 mmol) of 1'[3-(S)-(3,4-dichlorophenyl)-4-(t-butoxycarbonyl(methylamino))butyl]-spiro[(3-indanone)-1,4'-piperidine] with TFA and anisole according to the procedure of example 39, step A furnished 0.56 g of the title compound which was sufficiently pure for use in step B.

Step B: 1'[3-(S)-(3,4-dichlorophenyl)-4-(N-(3,5-dichloro) benzoyl-(methylamino))butyl]-spiro[(3-indanone)-1,4'-piperidine]

Reaction of 95 mg (0.22 mmol) of 1'[3-(S)-(3,4-dichlorophenyl)-4-(methylamino)butyl]-spiro[(3-indanone)-1,4'-piperidine] from step A above, with 3,5-dichlorobenzoyl chloride by the procedure of example 39 step B gave the title compound which was purified by prep TLC. Mass Spectrum (FAB) 607 ($^{37}Cl+^{35}Cl$ isotope), 605 ($^{35}Cl+^{35}Cl$ isotope).

The following compounds were prepared by substituting the required acid chloride for 3,5-dichlorobenzoyl chloride in step B.

EXAMPLE 67

1'-[3-(S)-(3,4-dichlorophenyl)-4-(N-(3-chloro-5-methyl) benzoyl-(methylamino))butyl]-spiro[(3-indanone)-1,4'-piperidine]

Mass Spectrum (FAB) 584 ($^{37}Cl+^{35}Cl$ isotope), 582 ($^{35}Cl+^{35}Cl$ isotope).

EXAMPLE 68

1'-[3-(S)-(3,4-dichlorophenyl)-4-(N-(3-fluoro-5-methyl) benzoyl-(methylamino))butyl]-spiro[(3-indanone)-1,4'-piperldine]

Mass Spectrum (FAB) 622 ($^{37}Cl+^{35}Cl$ isotope), 620 ($^{35}Cl+^{35}Cl$ isotope).

EXAMPLE 69

1'-[3-(S)-(3,4-dichlorophenyl)-4-(1-naphthoyl (methylamino))butyl]-spiro[(3-indanone)-1,4'-piperidine]

Mass Spectrum (FAB) 587 ($^{37}Cl+^{35}Cl$ isotope), 585 ($^{35}Cl+^{35}Cl$ isotope).

EXAMPLE 70

1'-[3-(S)-(3,4-dichlorophenyl)-4-(N-(3,5-dimethyl)benzoyl-(methylamino))butyl]-spiro[(3-hydroxy)indane)-1,4'-piperidine]

A solution of 0.384 g (0.68 mmol) of 1'[3-(S)-(3,4-dichlorophenyl)-4-((3,5-dimethyl)benzoyl(methylamino)) butyl]-spiro[(3-indanone)-1,4'-piperidine] (example 64) in 3 mL of methanol was treated with 13 mg (0.34 mmol) of NaBH4. Two additional 13 mg (0.34 mmol) portions of NaBH4 were added after 45 min intervals and the mixture was stirred another 45 min. The excess NaBH4 was destroyed by adding few drops of 10% HCl, diluted with water and the mixture was extraced with EtOAc. The organic phase was washed with water, brine and dried with Na2SO4. The residue after concentration of the filtrate was chromatographed on a flash column to isolate 0.313 g (81% yield) of the title compound. Mass Spectrum (FAB) 567 ($^{37}Cl+^{35}Cl$ isotope), 565 ($^{35}Cl+^{35}Cl$ isotope).

EXAMPLE 71

1'-[3-(S)-(3,4-dichlorophenyl)-4-(N-(3,5-dimethyl)benzoyl-(methylamino))butyl]-spiro[(3-acetyloxy)indane)-1,4'-piperidine]

The title compound was obtained by acylation of 1'[3-(S)-(3,4-dichlorophenyl)-4-((3,5-dimethyl)benzoyl (methylamino))butyl]-spiro[(3-hydroxy)indane)-1,4'-piperidine] (example 70) with acetyl chloride and Et3N in CH2Cl2. Mass Spectrum (FAB) 609 ($^{37}Cl+^{35}Cl$ isotope), 607 ($^{35}Cl+^{35}Cl$ isotope).

EXAMPLE 72

1'-[3-(S)-(3,4-dichlorophenyl)-4-(N-(3,5-dimethyl)benzoyl-(methylamino))butyl]-spiro[(3-methylamino-carbonyl-amino)indane-1,4'-piperidine]

Reductive amination of 3-(S)-(3,4-dichlorophenyl)-4-((3,5-dimethyl)benzoyl(methylamino))butanal (75 mg, 0.2 mmol) and spiro[(3-methylamino-carbonyl-amino)indane-1,4'-piperidine] (53 mg, 0.22 mmol) by the procedure of example 62 furnished 70 mg (57% yield) of the title compound. Mass Spectrum (FAB) 623 ($^{37}Cl+^{35}Cl$ isotope), 621 ($^{35}Cl+^{35}Cl$ isotope).

The following compounds were prepared by reacting the appropriate aldehyde with spiro[(3-ethoxycarbonyl)indane-1,4'-piperidine] according to the procedure of Example 62.

EXAMPLE 73

1'-[3-(S)-(3,4-dichlorophenyl)-4-(N-(3,5-bistrifluoromethyl)benzoyl-(methylamino))butyl]-spiro[(3-ethoxycarbonyl)indane)-1,4'-piperidine]

Mass Spectrum (FAB) 729($^{37}Cl+^{35}Cl$ isotope), 727 ($^{35}Cl+^{35}Cl$ isotope).

EXAMPLE 74

1'-[3-(S)-(3,4-dichlorophenyl)-4-(benzoyl(methylamino)) butyl]-spiro[(3-ethoxycarbonyl)indane)-1,4'-piperidine]

Mass Spectrum (FAB) 593($^{37}Cl+^{35}Cl$ isotope), 591($^{35}Cl+^{35}Cl$ isotope).

EXAMPLE 75

1'-(3-((S)-(3-Chlorophenyl))-4-(N-(phenylsulfonyl) (methylamino))-butyl)-spiro(indan-1-one-3,4'-piperidine)

A mixture of 3-((S)-(3-chlorophenyl))-4-(N-(phenylsulfonyl)(methylamino))butanal (30 mg, 0.085 mmol) (prepared according to the procedure of Hale, J. J.; Finke, P. E.; MacCoss, M. *Bioorganic Medicinal Chemistry Letters* 1993,3, 319–322 and Example 13 except using phenylsulfonyl chloride in place of the benzoyl chloride in the acylation), spiro(indan-1-one-3,4'-piperidine) (26 mg, 0.128 mmol), 4A molecular sieves (25 mg) and acetic acid (0.008 mL, 0.128 mmol) in THF (1 mL) was stirred at rt for 10 min. Sodium triacetoxyborohydride (36 mg, 0.17 mmol) was then added and the reaction was stirred at rt for 16 h. The mixture was poured into a water containing excess sodium carbonate and was extracted twice with ethyl acetate. The organic layers were washed with brine, dried, combined and concentrated in vacuo. The residue was purified by prep TLC using 5% methanol in methylene chloride as eluent to afforded the title compound (44 mg). Mass Spectrum ($NH_3$/Cl) M+H=537, 539

EXAMPLE 76

1'-(3-((S)-(3-Chlorophenyl))-4-(N-(phenylsulfonyl)(methylamino))-butyl)-spiro(1-hydroxyindane-3,4'-piperidine)

To a solution of 1'-(3-((S)-(3-chlorophenyl))-4-(N-(phenylsulfonyl)(methylamino))butyl)-spiro(indan-1-one-3,4'-piperidine) (12 mg, 0.021 mmol) prepared in Example 75 in methanol (0.7 mL) was added sodium borohydride (3×2 mg, 0.15 mmol) over 2 days until TLC indicated that the reaction was complete. The reaction was then quenched with water and extracted twice with ethyl acetate. The organic layers were washed with brine, dried over sodium sulfate, combined and concentrated in vacuo. The residue was purified by prep TLC eluting with 5% methanol in methylene chloride to afford the title compound (8.2 mg). Mass Spectrum (ESI) M+H=539, 541

EXAMPLE 77

1'-(3-((S)-(3-Chlorophenyl))-4-(N-(phenylsulfonyl)(methylamino))-butyl)-spiro(indane-1,4'-piperidine)

A mixture of 3-((S)-(3-chlorophenyl))-4-(N-(phenylsulfonyl)(methylamino))butanal (35 mg, 0.099 mmol), spiro(indane-1,4'-piperidine) hydrochloride (33 mg, 0.149 mmol), 4A molecular sieves (25 mg) and DIPEA (0.016 mL, 0.149 mmol) in THF (1 mL) was stirred at rt for 10 min. Sodium triacetoxyborohydride (42 mg, 0.20 mmol) was then added and the reaction was stirred at rt for 16–40 h. The mixture was poured into a water containing excess sodium carbonate and was extracted three times with ethyl acetate. The organic layers were washed with brine, dried, combined and concentrated in vacuo. The residue was purified by prep TLC using 5% methanol in methylene chloride as eluent to afforded the title compound (36 mg). Mass Spectrum ($NH_3$/Cl) M+H=523, 525

EXAMPLE 78

1'-(3-((S)-(3-Chlorophenyl))-4-(N-(phenylsulfonyl)(methylamino))-butyl)-spiro(6-methoxyindan-1-one-2 4'-piperidine)

A mixture of 3-((S)-(3-chlorophenyl))-4-(N-(phenylsulfonyl)(methylamino))butanal (20 mg, 0.057 mmol), spiro(6-methoxyindan-1-one-2,4'-piperidine) hydrochloride (22 mg, 0.085 mmol), 4A molecular sieves (25 mg) and DIPEA (0.009 mL, 0.085 mmol) in THF (1 mL) was stirred at rt for 10 min. Sodium triacetoxyborohydride (24 mg, 0.114 mmol) was then added and the reaction was stirred at rt for 16–40 h. The mixture was poured into a water containing excess sodium carbonate and was extracted three times with ethyl acetate. The organic layers were washed with brine, dried, combined and concentrated in vacuo. The residue was purified by prep TLC using 7% methanol in methylene chloride as eluent to afforded the title compound (31 mg). Mass Spectrum (ESI) M+H=567, 569

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method for treating infection by HIV, delaying of the onset of AIDS, or treating AIDS comprising the administration to a patient in need thereof of an effective amount of a compound of the formula:

I

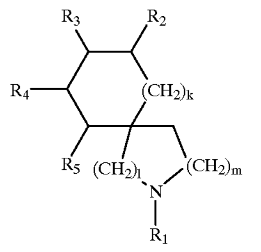

wherein the nitrogen atom expressly shown above is optionally quaternized with $C_{1-4}$alkyl or phenyl$C_{1-4}$alkyl or is optionally present as the N-oxide ($N^+O^-$), and wherein:

k is 0, 1 or 2;

l and m are each independently 0, 1, 2, 3, 4, or 5, with the proviso that the sum of 1+m is equal to 1, 2, 3, 4, or 5;

$R_1$ is selected from a group consisting of:

(1) hydrogen, and (2) linear or branched $C_{1-8}$ alkyl, linear or branched $C_{2-8}$ alkenyl, or linear or branched $C_{2-8}$ alkynyl, wherein the $C_{1-8}$ alkyl, $C_{2-8}$ alkenyl or $C_{2-8}$ alkynyl is optionally mono, di, tri or tetra substituted, the substitutents independently selected from:

(a) hydroxy, (b) oxo, (c) cyano, (d) halogen, wherein halogen is selected from: Br, Cl, I, or F, (e) trifluoromethyl, (f) phenyl or naphthyl or mono, di or trisubstituted phenyl or naphthyl, the substitutents independently selected from (1') hydroxy, (2') oxo, (3') phenyl, (4') $C_{1-3}$alkyl, (5') cyano, (6') halogen, (7') trifluoromethyl, (8') —$NR_6COR_7$, wherein $R_6$ and $R_7$ are independently selected from:

(a') hydrogen, (b') $C_{1-6}$ alkyl, or mono or disubstituted $C_{1-6}$ alkyl, the substitutents independently selected from:

(1") phenyl, (2") hydroxy, (3") oxo, (4") cyano, (5") halogen, or (6") trifluoromethyl, (c') phenyl or naphthyl or mono di or trisubstituted phenyl or naphthyl, the substitutents independently selected from:

(1") hydroxy,
(2") $C_{1-3}$alkyl,
(3") cyano,
(4") halogen, or
(5") trifluoromethyl, or
(d') $C_{1-3}$alkyloxy,
or $R_6$ and $R_7$ are joined together with the nitrogen to which they are attached to form a 5-, 6-, or 7-membered monocyclic saturated ring containing 1 or 2 heteroatoms independently selected from nitrogen, oxygen, or sulfur, and in which the ring is unsubstituted or mono or disubstituted, the substituents independently selected from
(1") hydroxy,
(2") oxo,
(3") cyano,
(4") halogen, or
(5") trifluoromethyl,
(9') —$NR_6CO_2R_7$,
(10') —$NR_6CONHR_7$,
(11') —$NR_6S(O)_jR_7$, wherein j is 1 or 2,
(12') —$CONR_6R_7$,
(13') —$COR_6$,
(14') —$CO_2R_6$,
(15') —$OR_6$,
(16') —$S(O)_iR_6$, wherein i is 0, 1, or 2, or
(17') heteroaryl, wherein heteroaryl is selected from the group consisting of:
(1") benzimidazolyl,
(2") benzofuranyl,
(3") benzooxazolyl,
(4") furanyl,
(5") imidazolyl,
(6") indolyl,
(7") isooxazolyl,
(8") isothiazolyl,
(9") oxadiazolyl,
(10") oxazolyl,
(11") pyrazinyl,
(12") pyrazolyl,
(13") pyridyl,
(14") pyrimidyl,
(15") pyrrolyl,
(16") quinolyl,
(17") tetrazolyl,
(18") thiadiazolyl,
(19") thiazolyl,
(20") thienyl, and
(21") triazolyl,
wherein the heteroaryl is unsubstituted or mono di or trisubstituted, the substituents independently selected from:
(a") hydroxy,
(b") oxo,
(c") cyano,
(d") halogen, or
(e") trifluoromethyl,
(g) —$NR_6R_7$,
(h) —$NR_6COR_7$,
(i) —$NR_6CO_2R_7$,
(j) —$NR_6CONHR_7$,
(k) —$NR_6S(O)_jR_7$,
(l) —$CONR_6R_7$,
(m) —$COR_6$,
(n) —$CO_2R_6$,
(o) —$OR_6$,
(p) —$S(O)_iR_6$, or (q) heteroaryl, wherein heteroaryl is defined above;
wherein the nitrogen of definition —$NR_6R_7$ above is optionally quaternized with $C_{1-4}$alkyl or phenyl$C_{1-4}$alkyl or is optionally present as the N-oxide ($N^+O^-$);
$R^2$, $R^3$, $R^4$, and $R^5$ are independently selected from the group consisting of:
(1) hydrogen;
(2) hydroxy;
(3) oxo; and
(4) —$NR_6R_7$ or —$NR_6C(O)$—$NR_6R_7$, wherein the nitrogen of —$NR_6R_7$ is optionally quaternized with $C_{1-4}$alkyl or phenyl$C_{1-4}$alkyl or is optionally present as the N-oxide,
or $R^2$ and $R^3$, or $R^3$ and $R^4$, together form a carbon-carbon bond, or $R^2$ and $R^3$, or $R^3$ and $R^4$, or $R^4$ and $R^5$ are joined to form a ring selected from the group consisting of:
(a) benzimidazolyl,
(b) benzofuranyl,
(c) benzooxazolyl,
(d) furanyl,
(e) imidazolyl,
(f) indolyl,
(g) isooxazolyl,
(h) isothiazolyl,
(i) naphthyl,
(j) oxadiazolyl,
(k) oxazolyl,
(l) phenyl
(m) pyrazinyl,
(n) pyrazolyl,
(o) pyridyl,
(p) pyrimidyl,
(q) pyrrolyl,
(r) quinolyl,
(s) thiadiazolyl,
(t) thiazolyl,
(u) thienyl, and
(v) triazolyl,
and wherein the ring is unsubstituted, mono, di or tri substituted, the substitutents selected from:
(1') $C_{1-6}$ linear or branched alkyl, unsubstituted or mono or disubstituted, the substituents being selected from hydrogen or hydroxy,
(2') $C_{2-6}$ linear or branched alkenyl,
(3') hydroxy
(4') oxo
(5') —$OR_6$,
(6') halogen,
(7') trifluoromethyl,
(8') nitro,
(9') cyano,
(10') —$NR^6R^7$,
(11') —$NR^6COR^7$,
(12') —$NR_6CO_2R^7$,
(13') —$NR_6CONHR^7$,
(14') —$NR_6S(O)_j$—$R_7$
(15') —$CONR^6R^7$,
(16') —$COR^6$,
(17') —$CO_2R^6$,
(18') —$S(O)_iR_6$, or
(19') heteroaryl, wherein heteroaryl is defined above;

X is carbon, or X—$R^5$ is oxygen or S—$(O)_i$;

or pharmaceutically acceptable salts thereof.

2. The method of claim 1 wherein the compound is of the Formula II:

I

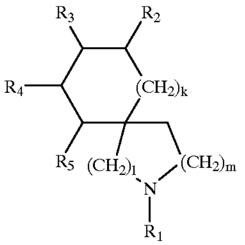

wherein k is 0 or 1;

the sum of l+m is 3;

$R_1$ is:

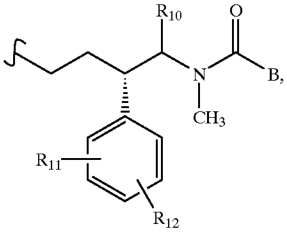

or

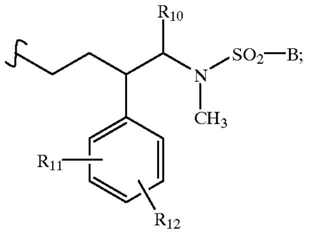

$R_2$ and $R_3$ are independently selected from: hydrogen, hydroxy, oxo, or $—NR_6C(O)R_7R_8$, wherein $R_6$, $R_7$ and $R_8$ are independently selected from:

(a) hydrogen, (b) $C_{1-6}$ alkyl, which is unsubstituted or mono or disubstituted, wherein the substitutents on alkyl are independently selected from: hydroxy, halo, trifluoromethyl, $C_{1-3}$alkyl, or phenyl; or (c) phenyl, unsubstituted or mono or disubstituted, the substituents on phenyl are independently selected from: hydroxy, halo, trifluoromethyl, $C_{1-3}$alkyl or phenyl;

B is selected from:

(a) phenyl, naphthyl, mono di or trisubstituted phenyl, or mono di or trisubstituted naphthyl, wherein the substitutents on phenyl or naphthyl are independently selected from:

chloro, methyl, phenyl or $CF_3$;

(b) $—CH_2$-phenyl, or mono or disubstituted $—CH_2$-phenyl, wherein the substitutents on phenyl are independently selected from:

fluoro, chloro, methyl, phenyl or $CF_3$;

(c) pyridyl, or mono, di or trisubstituted pyridyl, wherein the substitutents on pyridyl are independently selected from:

chloro, methyl, phenyl or $CF_3$; or (d) thiophene, or mono or disubstituted thiophene, wherein the substitutents on thiophene are independently selected from:

chloro, methyl, phenyl or $CF_3$;

$R_4$ and $R_5$ are joined together to form a ring selected from:

thiophene or substituted phenyl, wherein the substitutent on phenyl is selected from:

(a) hydrogen, (b) $CH_3O—$, (c) $CH_3SO_2NH—$, or (d) $CH_3SO_2—$;

$R_{10}$ is selected from: hydrogen, $C_{1-3}$alkyl, or phenyl;

$R_{11}$ and $R_{12}$ are independently selected from: hydrogen, halogen, methyl, phenyl or $CF_3$;

or pharmaceutically acceptable salts thereof.

3. The method of claim 1 wherein the compound is of the Formula II:

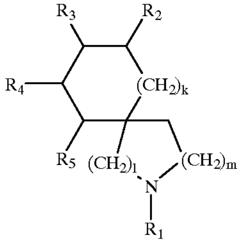

wherein:

k is 0 or 1;

the sum of l+m is 3;

$R_1$ is:

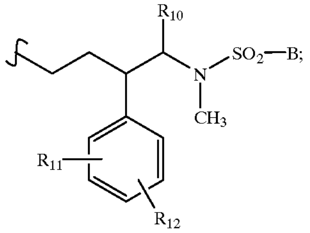

$R_2$ and $R_3$ are independently selected from:

hydrogen, hydroxy, oxo, or $—NR_6C(O)R_6R_7$;

B is selected from:

phenyl, mono or disubstituted phenyl, naphthyl, mono or disubstituted naphthyl, thiophene, or monosubstituted thiophene wherein the substitutent on phenyl, naphthyl or thiophene is selected from: $CF_3$, $CH_3$, Cl, F, or Br;

$R_4$ and $R_5$ are joined together to form a ring selected from:

thiophene or substituted phenyl, wherein the substitutent on phenyl is selected from:

(a) hydrogen, (b) $CH_3O—$, (c) $CH_3SO_2NH—$, or (d) $CH_3SO_2—$;

$R_{10}$ is hydrogen, $C_{1-3}$alkyl or phenyl;

$R_{11}$ and $R_{12}$ are independently selected from:

hydrogen, chloro, methyl, phenyl or $CF_3$;

or pharmaceutically acceptable salts thereof.

4. The method of claim 3 wherein B is unsubstituted phenyl, 3-chlorophenyl, 3-fluorophenyl or unsubstituted thiophene.

5. The method of claim 1 wherein the compound is of the Formula III:

III

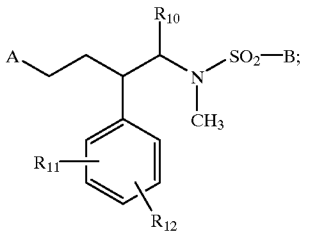

wherein A is selected from:

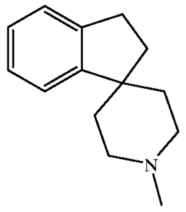 ,

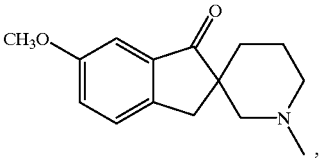 ,

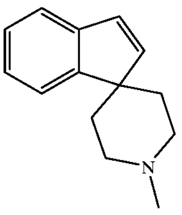 ,

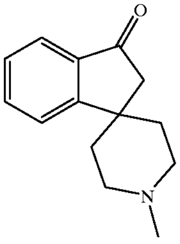 ,

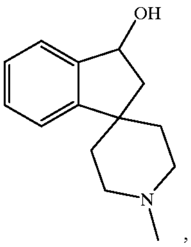 , or

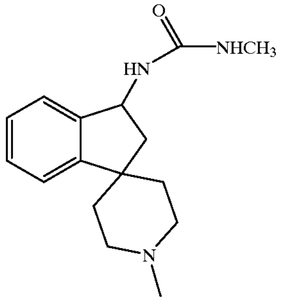 ;

B is selected from:

phenyl, mono or disubstituted phenyl, thiophene, or monosubstituted thiophene wherein the substitutent on phenyl or thiophene is selected from:

$CF_3$, $CH_3$, Cl, F, or Br;

$R_{11}$ and $R_{12}$ are independently selected from:

hydrogen, chloro, methyl, phenyl or $CF_3$;

or pharmaceutically acceptable salts thereof.

6. The method of claim 5 wherein B is unsubstituted phenyl, 3-chlorophenyl, 3-fluorophenyl or unsubstituted thiophene.

7. The method of claim 5 wherein A is:

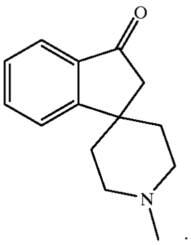 .

8. The method of claim 5 wherein $R_{11}$ and $R_{12}$ are chloro.

9. The method of claim 1 wherein the compound is selected from the group consisting of:

1'-(3(S)-(3,4-dichlorophenyl)-4-(N-methyl)benzamidobutyl)spiro(1H-indene-1,4'-piperidine);

1'-(3(S)-(3,4-dichlorophenyl)-4-((N-methyl)-3,5-bis(trifluoromethyl)benzamidobutyl)spiro(1H-indene-1,4'-piperidine);

1'-((3S)-(3,4-dichlorophenyl)-4-(N-methyl)benzamidobutyl)-3,4-dihydro-4-hydroxy-6-methoxy-spiro[2H-1-benzopyran-2,3'-piperidine];

1'-((3S)-(3,4-dichlorophenyl)-4-(N-methyl)benzamidobutyl)-3,4-dihydro-4-hydroxy-6-methoxy-spiro[2H-1-benzopyran-2,4'-piperidine];

1'-((3S)-(3,4-dichlorophenyl)-4-(N-methyl)benzamidobutyl)spiro(indane-1,4'-piperidine);

1'-(1-oxo-(3S)-(3,4-dichlorophenyl)-4-(N-methyl)-benzamidobutyl)spiro(1H-indene-1,4'-piperidine);

1'-((3S)-(3,4-dichlorophenyl)-(4)-((N-methyl) benzamido)-pentyl)spiro(1H-indene-1,4'-piperidine);

1'-((2)-((3S)-(3,4-dichlorophenyl)-5-(N-methyl)-benzamido)pentyl)spiro(1-indane-1,4'-piperidine);

1'-((3S)-(3,4-dichlorophenyl)-(4)-((N-methyl) benzamido)octyl)spiro(1H-indene-1,4'-piperidine);

1'-((4)-((3S)-(3,4-dichlorophenyl)-1-(N-methyl)-benzamido)octyl)spiro(1H-indene-1,4'-piperidine);

1'-((3S)-(3,4-dichlorophenyl)-4-((N-methyl)benzenesulfonamidobutyl)spiro[1H-indene-1,4'-piperidine];

1'-((3S)-(3,4-dichlorophenyl)-4-((N-methyl)furan-2-carboxamidobutyl)spiro[1H-indene-1,4'-piperidine];

1'-((3S)-(3,4-dichlorophenyl)-4-((N-methyl)phenoxycarboxamidobutyl)spiro[1H-indene-1,4'-piperidine];

1'-((3S)-(3,4-dichlorophenyl)-4-((N-methyl)phenylaminocarboxamidobutyl)spiro[1H-indene-1,4'-piperidine];

1'-((3S)-(3,4-dichlorophenyl)-4-((N-methyl)pyridine-2-carboxamidobutyl)spiro[1H-indene-1,4'-piperidine];

1'-((3S)-(3,4-dichlorophenyl)-4-((N-methyl)pyridine-3-carboxamidobutyl)spiro[1H-indene-1,4'-piperidine];

1'-((3S)-(3,4-dichlorophenyl)-4-((N-methyl)pyridine-4-carboxamidobutyl)spiro[1H-indene-1,4'-piperidine];

1'-((3S)-(3,4-dichlorophenyl)-4-((N-methyl)benzothiophene-2-carboxamidobutyl)spiro[1H-indene-1,4'-piperidine];

1'-((3S)-(3,4-dichlorophenyl)-4-((N-methyl)thiophene-2-acetamidobutyl)spiro[1H-indene-1,4'-piperidine];

1'-((3S)-(3,4-dichlorophenyl)-4-((N-methyl)thiophene-3-carboxamidobutyl)spiro[1H-indene-1,4'-piperidine];

1'-((3S)-(3,4-dichlorophenyl)-4-((N-methyl)-(3-methylthiophene-2-carboxamido)butyl)spiro[1H-indene-1,4'-piperidine];

1'-((3S)-(3,4-dichlorophenyl)-4-((N-methyl)-(5-methyl-thiophene-2-carboxamido)butyl)spiro[1H-indene-1,4'-piperidine];

1'-((3S)-(3,4-dichlorophenyl)-4-((N-methyl)-(5-chloro-thiophene-2-carboxamido)butyl)spiro[1H-indene-1,4'-piperidine];

1'-((3S)-(3,4-dichlorophenyl)-4-((N-methyl)-(2,3-dibromo-thiophene-5-carboxamido)butyl)spiro[1H-indene-1,4'-piperidine];

1'-[-(S)-(3,4-dichlorophenyl)-4-(t-butoxycarbonyl (methyl-amino))butyl]-spiro(1H-indene-1,4'-piperidine);

1'-[3-(S)-(3,4-dichlorophenyl)-4-(N-(3,5-dichloro) benzoyl-(methylamino))butyl]-spiro(1H-indene-1,4'-piperidine);

1'-[3-(S)-(3,4-dichlorophenyl)-4-(N-(3-chloro)benzoyl-(methylamino))butyl]-spiro(1H-indene-1,4'-piperidine);

1'-[3-(S)-(3,4-dichlorophenyl)-4-(N-(3-trifluoromethyl)-benzoyl-(methylamino))butyl]-spiro(1H-indene-1,4'-piperidine);

1'-[3-(S)-(3,4-dichlorophenyl)-4-(N-(3-isopropyloxy)-benzoyl-(methylamino))butyl]-spiro(1H-indene-1,4'-piperidine);

1'-[3-(S)-(3,4-dichlorophenyl)-4-(N-(3-isopropyloxy)-phenylacetyl-(methylamino))butyl]-spiro(1H-indene-1,4'-piperidine);

1'-[3-(S)-(3,4-dichlorophenyl)-4-(N-(4-t-butyl)benzoyl-(methylamino))butyl]-spiro(1H-indene-1,4'-piperidine;

1'-[3-(S)-(3,4-dichlorophenyl)-4-(N-(2-phenyl)benzoyl-(methylamino))butyl]-spiro(1H-indene-1,4'-piperidine);

1'-[3-(S)-(3,4-dichlorophenyl)-4-(N-(1-naphthoyl-(methylamino))butyl]-spiro(1H-indene-1,4'-piperidine);

1'-[3-(S)-(3,4-dichlorophenyl)-4-(N-(2-naphthoyl-(methylamino))butyl]-spiro(1H-indene-1,4'-piperidine);

1'-[3-(S)-(3,4-dichlorophenyl)-4-(N-(2-methyl)benzoyl-(methylamino))butyl]-spiro(1H-indene-1,4'-piperidine);

1'-[3-(S)-(3,4-dichlorophenyl)-4-(N-(4-methyl)benzoyl-(methylamino))butyl]-spiro(1H-indene-1,4'-piperidine);

1'-[3-(S)-(3,4-dichlorophenyl)-4-(N-(3-methyl)benzoyl-(methylamino))butyl]-spiro(1H-indene-1,4'-piperidine);

1'-[3-(S)-(3,4-dichlorophenyl)-4-(N-(3,5-dimethyl) benzoyl-(methylamino))butyl]-spiro(1H-indene-1,4'-piperidine);

1'-[3-(S)-(3,4-dichlorophenyl)-4-(N-(2,3-dimethyl) benzoyl-(methylamino))butyl]-spiro(1H-indene-1,4'-piperidine);

1'-[3-(S)-(3,4-dichlorophenyl)-4-(N-(3,4-dimethyl) benzoyl-(methylamino))butyl]-spiro(1H-indene-1,4'-piperidine);

1'-[3-(S)-(3,4-dichlorophenyl)-4-(N-(2,5-dimethyl) benzoyl-(methylamino))butyl]-spiro(1H-indene-1,4'-piperidine);

1'-[3-(S)-(3,4-dichlorophenyl)-4-(N-(2,4-dimethyl) benzoyl-(methylamino))butyl]-spiro(1H-indene-1,4'-piperidine);

1'-[3-(S)-(3,4-dichlorophenyl)-4-(trifluoroacetyl-(methylamino))butyl]-spiro(1H-indene-1,4'-piperidine);

1'-[3-(S)-(3,4-dichlorophenyl)-4-(t-butylcarbonyl-(methylamino))butyl]-spiro(1H-indene-1,4'-piperidine);

1'-[3-(S)-(3,4-dichlorophenyl)-4-(1-adamentanecarbonyl-(methylamino))butyl]-spiro(1H-indene-1,4'-piperidine);

1'-[3-(S)-(3,4-dichlorophenyl)-4-(cyclohexanecarbonyl-(methylamino))butyl]-spiro(1H-indene-1,4'-piperidine);

1'-[3-(S)-(3,4-dichlorophenyl)-4-(N-(3-methyl)benzoyl-(methylamino))butyl]-spiro[indane-1,4'-piperidine];

1'-[3-(S)-(3,4-dichlorophenyl)-4-(N-(3,5-dimethyl) benzoyl-(methylamino))butyl]-spiro[indane-1,4'-piperidine];

1'-[3-(S)-(3,4-dichlorophenyl)-4-(N-(3,5-bistrifluoro-methyl)benzoyl-(methylamino))butyl]-spiro[(3-indanone)-1,4'-piperidine];

1'-[3-(S)-(3,4-dichlorophenyl)-4-(N-benzoyl-(methyl-amino))butyl]-spiro[(3-indanone)-1,4'-piperidine];

1'-[3-(S)-(3,4-dichlorophenyl)-4-(N-(3,5-dimethyl) benzoyl-(methylamino))butyl]-spiro[(3-indanone)-1,4'-piperidine];

1'-[3-(S)-(3,4-dichlorophenyl)-4-(t-butoxycarbonyl-(methylamino))butyl]-spiro[(3-indanone)-1,4'-piperidine];

1'-[3-(S)-(3,4-dichlorophenyl)-4-(N-(3,5-dichloro) benzoyl-(methylamino))butyl]-spiro[(3-indanone)-1,4'-piperidine];

1'-[3-(S)-(3,4-dichlorophenyl)-4-(N-(3-chloro-5-methyl)-benzoyl(methylamino))butyl]-spiro[(3-indanone)-1,4'-piperidine];

1'-[3-(S)-(3,4-dichlorophenyl)-4-(N-(3-fluoro-5-methyl)-benzoyl-(methylamino))butyl]-spiro[(3-indanone)-1,4'-piperidine];

1'-[3-(S)-(3,4-dichlorophenyl)-4-(1-naphthoyl(methyl-amino))butyl]-spiro[(3-indanone)-1,4'-piperidine];

1'-[3-(S)-(3,4-dichlorophenyl)-4-(N-(3,5-dimethyl) benzoyl-(methylamino))butyl]-spiro[(3-hydroxy) indane)-1,4'-piperidine];

1'-[3-(S)-(3,4-dichlorophenyl)-4-(N-(3,5-dimethyl) benzoyl-(methylamino))butyl]-spiro[(3-acetyloxy) indane)-1,4'-piperidine];

1'-[3-(S)-(3,4-dichlorophenyl)-4-(N-(3,5-dimethyl) benzoyl-(methylamino))butyl]-spiro[(3-methylamino-carbonyl-amino)indane-1,4'-piperidine];

1'-[3-(S)-(3,4-dichlorophenyl)-4-(N-(3,5-bistrifluoro-methyl)benzoyl-(methylamino))butyl]-spiro[(3-ethoxycarbonyl)indane)-1,4'-piperidine];

1'-[3-(S)-(3,4-dichlorophenyl)-4-(benzoyl (methylamino))-butyl]-spiro[(3-ethoxycarbonyl) indane)-1,4'-piperidine];

1'-(3-((S)-(3-chlorophenyl))-4-(N-(phenylsulfonyl) (methyl-amino))-butyl)-spiro(indan-1-one-3,4'-piperidine);

1'-(3-((S)-(3-chlorophenyl))-4-(N-(phenylsulfonyl)(methyl-amino))-butyl)-spiro(1-hydroxyindane-3,4'-piperidine);

1'-(3-((S)-(3-Chlorophenyl))-4-(N-(phenylsulfonyl)(methyl-amino))-butyl)-spiro(indane-1,4'-piperidine); and 1'-(3-((S)-(3-Chlorophenyl))-4-(N-(phenylsulfonyl)(methyl-amino))-butyl)-spiro(6-methoxyindan-1-one-2,4'-piperidine);

and pharmaceutically acceptable salts thereof.

* * * * *